US008829145B2

(12) United States Patent
Tulloch et al.

(10) Patent No.: US 8,829,145 B2
(45) Date of Patent: Sep. 9, 2014

(54) WATER-STABLE CATALYSTS FOR POLYURETHANE MANUFACTURE

(75) Inventors: Arran Alexander Dickon Tulloch, Northallerton (GB); David Jenkins, Stockton on Tees (GB); Joseph Atkinson, Middlesbrough (GB); Mark Alexander Kent, Selby (GB); Alan Cooper, Wingate (GB)

(73) Assignee: Dorf Ketal Chemicals (India) Pvt. Ltd., Mumbai (IN)

( * ) Notice: Subject to any disclaimer, the term of this patent is extended or adjusted under 35 U.S.C. 154(b) by 102 days.

(21) Appl. No.: 12/665,377

(22) PCT Filed: Jun. 16, 2008

(86) PCT No.: PCT/GB2008/050451
§ 371 (c)(1),
(2), (4) Date: Jun. 8, 2010

(87) PCT Pub. No.: WO2008/155569
PCT Pub. Date: Dec. 24, 2008

(65) Prior Publication Data
US 2010/0249359 A1 Sep. 30, 2010

(30) Foreign Application Priority Data

Jun. 18, 2007 (GB) .................................. 0711734.4
Nov. 16, 2007 (GB) .................................. 0722462.9

(51) Int. Cl.
C08G 18/22 (2006.01)
B01J 31/12 (2006.01)
C07C 215/14 (2006.01)
C07F 7/00 (2006.01)
C08G 18/10 (2006.01)
C08G 18/12 (2006.01)
C08G 18/08 (2006.01)
C08G 101/00 (2006.01)

(52) U.S. Cl.
CPC ............... *C07F 7/006* (2013.01); *C07C 215/14* (2013.01); *C08G 2101/0083* (2013.01); *B01J 2531/0238* (2013.01); *C08G 18/222* (2013.01); *C08G 18/10* (2013.01); *C08G 18/12* (2013.01); *C08G 18/0885* (2013.01); *B01J 2531/46* (2013.01)
USPC .................. 528/51; 528/56; 528/55; 528/52; 502/155

(58) Field of Classification Search
CPC .................................. C08G 18/22; B01J 31/12
See application file for complete search history.

(56) References Cited

U.S. PATENT DOCUMENTS

| 2,824,115 | A | | 2/1958 | Beacham et al. |
| 2,985,685 | A | | 5/1961 | Thomas et al. |
| 3,121,012 | A | | 2/1964 | Agruss |
| 3,131,062 | A | | 4/1964 | Agruss |
| 3,245,776 | A | * | 4/1966 | Rubin ................................ 71/1 |
| 3,294,689 | A | | 12/1966 | Pierce |
| 3,558,264 | A | * | 1/1971 | Habib ............................ 8/127.6 |
| 3,838,070 | A | | 9/1974 | Thomas |
| 4,142,061 | A | | 2/1979 | Wilkes |
| 4,325,740 | A | | 4/1982 | Jacobson |
| 4,540,781 | A | | 9/1985 | Barsa |
| 4,568,703 | A | | 2/1986 | Ashida |
| 4,798,902 | A | | 1/1989 | Putzig |
| 5,217,838 | A | | 6/1993 | Wilson et al. |
| 5,225,248 | A | * | 7/1993 | Stephenson ................... 427/333 |
| 5,902,835 | A | * | 5/1999 | Meier et al. ................... 521/125 |
| 6,525,227 | B1 | | 2/2003 | Kobayashi |

FOREIGN PATENT DOCUMENTS

| EP | 0 169 707 A2 | 1/1986 |
| EP | 0 169 707 A3 | 1/1986 |
| EP | 0 278 684 A1 | 8/1988 |
| EP | 0 368 911 B1 | 5/1990 |
| EP | 0 544 290 A2 | 6/1993 |
| GB | 755728 | 8/1956 |
| GB | 767644 | 2/1957 |
| GB | 786388 | 11/1957 |
| GB | 1 038 186 | 8/1966 |
| GB | 2 207 426 A | 2/1989 |
| JP | 63-97952 A | 4/1988 |
| JP | 63-97953 A | 4/1988 |
| JP | 2000-128948 A | 5/2000 |
| WO | WO-92/20463 A1 | 11/1992 |

(Continued)

OTHER PUBLICATIONS

BORAX Detergent Book. 2005.*

(Continued)

*Primary Examiner* — Randy Gulakowski
*Assistant Examiner* — Jeffrey Washville
(74) *Attorney, Agent, or Firm* — Conley Rose, P.C.; Rodney B. Carroll

(57) ABSTRACT

A method of manufacturing a polyurethane compound comprises mixing together a polyol, a polyisocyanate compound and a catalyst and allowing the mixture to cure to form a polyurethane, and is characterized in that the catalyst is a neutral complex of a metal selected from Ti, Zr, Hf, Al, Fe, Bi or Sn and a multidentate organic ligand having: a) a number of anionic donor sites=x; b) a number of neutral donor sites, capable of forming a co-ordinate bond with the metal, =y; c) where x+y=from 5 to 8; d) x is from 2 to 4; e) the ligand molecule is of a size and conformation to enable each of the anionic donor sites and neutral donor sites to form a bond with the same metal atom.

33 Claims, 6 Drawing Sheets

(56) References Cited

FOREIGN PATENT DOCUMENTS

| WO | WO-01/39885 A1 | 6/2001 |
|---|---|---|
| WO | WO-2006/106366 A1 | 10/2006 |
| WO | WO-2007/095018 A2 | 8/2007 |
| WO | WO-2007/095018 A3 | 8/2007 |
| WO | WO-2007/095367 A2 | 8/2007 |
| WO | WO-2008/082504 A1 | 7/2008 |

OTHER PUBLICATIONS

Mba et al., "$C_3$-Symmetric Ti(IV) Triphenolate Amino Complexes as Sulfoxidation Catalysts with Aqueous Hydrogen Peroxide," *Organic Letters*, 2007, vol. 9, No. 1, pp. 21-24.

Peri et al., "Distinctive structural features of hydroxyamino-1,3,5-triazine ligands leading to enhanced hydrolytic stability of their titanium complexes," *Dalton Transactions*, 2006, pp. 4169-4172.

Buonomenna et al., "Ti(IV)-based catalytic membranes for efficient and selective oxidation of secondary amines," *Tetrahedron Letters*, 2004, vol. 45, pp. 7515-7518.

Kim et al., "Novel Titanatranes with Different Ring Sizes: Syntheses, Structures, and Lactide Polymerization Catalytic Capabilities," *Organometallics*, 2002, vol. 21, No. 12, pp. 2395-2399.

Kobayashi et al., "Green Lewis acid catalysis in organic synthesis," *Pure Appl. Chem.*, 2000, vol. 72, No. 7, pp. 1373-1380.

Kobayashi et al., "Lewis Acid Catalysts Stable in Water. Correlation between Catalytic Activity in Water and Hydrolysis Constants and Exchange Rate Constants for Substitution of Inner-Sphere Water Ligands," *J. Am. Chem. Soc.*, 1998, vol. 120, pp. 8287-8288.

Kolarić et al., "Comparative study of C(2) epimerization of $_D$-glucose and $_D$-mannose catalyzed by water soluble organometallic complexes with nitrogen ligands," *Journal of Molecular Catalysis A: Chemical*, 1996, vol. 110, pp. 181-188.

Rammo et al., "Ligand and Cosubstrate Effects on the Hydrolysis of Phosphate Esters and DNA with Lanthanoids," *Liebigs Ann.*, 1996, pp. 1757-1767.

Evans et al, "Synthesis and X-ray Studies of the Seven-Coordinate $Ti^{IV}$(THPED) Dimer," *Polyhedron*, 1993, vol. 12, No. 3, pp. 337-341.

Hefele et al., "Komplexe mit N,N,N',N'-Tetrakis(2-hydroxybenzyl)ethylendiamin ($H_4$tben). Kristallstruktur von Ti(ben)," *Z. anorg. Allg. Chem.*, 1995, vol. 621, No. 4, pp. 671-674.

Sanderson, "Cleaner industrial processes using hydrogen peroxide," *Pure Appl. Chem.*, 2000, vol. 72, No. 7, pp. 1289-1304.

Wan et al., "TS-1 oxidation of aniine to azoxybenzene in a microstructured reactor," *Applied Catalysis A: General*, Mar. 18, 2005, vol. 281, Issues 1-2, pp. 285-293.

Hou et al., "Lanthanides in Organic Synthesis. Samarium Metal Promoted Selective Formation of Azoxy Compounds," *J. Org. Chem.*, 1988, 53 (13), pp. 3118-3120.

Bamoharram et al., "Catalytic performance of Preyssler heteropolyacid as a green and recyclable catalyst in oxidation of primary aromatic amines," *Journal of Molecular Catalysis A: Chemical*, vol. 255, Issues 1-2, Aug. 2006, pp. 193-198.

Hall et al., "Metal Ion Complexes of N,N'-Bis-(2-hydroxyethyl)-ethylenediamine. Reaction of the Copper (II) Complexes with Sodium Hydroxide," *J. Am. Chem. Soc.*, 1960, 82 (13), pp. 3300-3303.

Brown et al., "Chiral Synthesis via Organoboranes. 9. Crystalline "Chelates" from Borinic and Boronic Esters. A Simple Procedure for Upgrading Borinates and Boronates to Materials Approaching 100% Optical Purity," *J. Org. Chem.*, 1986, 51 (24), pp. 4526-4530.

Crans et al., "Characterization of Vanadium (V) Complexes in Aqueous Solutions: Ethanolamine- and Glycine-Derived Complexes," *J. Am. Chem. Soc.*, 1994, 116 (4), pp. 1305-1315.

Turan et al., "Steric Effects in Chelation Kinetics. III. Reactions of Aquonickel(II) Ion with N-Alkyl-Substituted Ethylenediamines," *Inorg. Chem.*, 1972, 11 (2), pp. 288-295.

Pearson et al, "Complexes of Nickel with N,N,N',N'-Tetrakis(2-hydroxyethyl)ethylenediamine," *Inorg. Chem.*, 1964, 3 (4), pp. 476-479.

Hall et al., "Metal Chelates of Alkanol-substituted Amines," *J. Am. Chem. Soc.*, 1960, 82 (13), pp. 3303-3308.

Hancock, "Macrocycles and their selectivity for metal ions on the basis of size," *Pure & Appl. Chem.*, 1986, vol. 58, No. 11, pp. 1445-1452.

Waghmode et al, "Liquid phase oxidation of amines to azoxy compounds over ETS-10 molecular sieves," *Green Chemistry*, 2001, 3, 285-288.

Wada et al, "Synthesis of new titanium chelated complexes stabilized in aqueous solution and their stability of pH and temperature," *Journal of Materials Science Letters*, Oct. 2000, vol. 19, No. 20, pp. 1855-1858.

Tofan et al., "Molecular structure of the seven coordinate aqua-(N-hydroxyethyl)ethylenediaminetriacetato titanium(III) and aqua-(N-ethoxo)ethylenediaminetriacetato titanium(IV)($Ti^{III}$(HEDTA)($H_2O$)]•$2H_2O$ and [$Ti^{IV}$(EEDTA)($H_2O$]•$2H_2O$)," *Inorganica Chimica Acta*, vol. 319, Issues 1-2, Jul. 16, 2001, pp. 63-66.

Li et al., "Ultra-Deep Desulfurization of Diesel: Oxidation with a Recoverable Catalyst Assembled in Emulsion," *Chemistry—A European Journal*, vol. 10 Issue 9, pp. 2277-2280.

* cited by examiner

Fig 3: End of Rise

WATER-STABLE CATALYSTS FOR POLYURETHANE MANUFACTURE

CROSS-REFERENCE TO RELATED APPLICATIONS

This application is the U.S. National Phase application of PCT International Application No. PCT/GB2008/050451, filed Jun. 16, 2008, and claims priority of British Patent Application Nos. 0711734.4, filed Jun. 18, 2007, and 0722462.9, filed Nov. 16, 2007, all of which are incorporated herein by reference.

FIELD OF THE INVENTION

The present invention concerns the use of certain metal-organic compounds, which are particularly stable to hydrolysis, as catalysts useful in the manufacture of polyurethane compounds.

BACKGROUND OF THE INVENTION

Polyurethane materials are made by reacting together a compound having more than one isocyanate function, i.e. a polyisocyanate, with a compound having more than one hydroxyl function, i.e. a polyol. In most cases a catalyst is added to the reaction mixture to accelerate the reaction and ensure complete and reproducible reaction conditions. A variety of catalysts is known and used for polyurethane manufacture, the most common being compounds of tin or mercury and also organic amine compounds. In many applications, metal catalysts are preferred because they are efficient and very effective. Whilst the use of heavy metal catalysts in polyurethane goods may not now be desirable, the alternative metals have disadvantages, particularly in shelf life and stability to hydrolysis. Titanium compounds, in particular, have the potential to offer economical alternatives which are of low toxicity compared with mercury for example. A problem with compounds of titanium and other metals such as aluminium, zirconium etc is that they are very effective catalysts but are rapidly hydrolysed in the presence of water to less catalytically active or inactive compounds.

Some polyurethane compounds, such as foams, are made from a reaction mixture to which a small percentage of water is added. Clearly in such a case the catalyst must be stable in the presence of water. In other cases the polyol composition of a two-part polyurethane reaction mixture contains water due to the hygroscopic nature of many polyols. It is common practice in the polyurethane supply chain to supply a two-part polyurethane formulation to an end-user in which the catalyst is already present, usually in the polyol-containing part. The user then mixes together the two parts and shapes the mixture before it cures to form a polyurethane material. The polyol, containing the catalyst, must therefore be stable during the period from manufacture to use and this may be a period of several months, depending on the application. If the catalyst/polyol mixture is not stable then changes in the catalyst activity can greatly affect the efficacy of the catalyst and thereby the properties of the cured polyurethane. It is therefore desirable to use as a catalyst a metal compound which is of relatively low toxicity compared with mercury or tin and which is stable in contact with a polyol over a long period of time, yet which is sufficiently active as a catalyst to be used in place of the currently used compounds.

It is an object of the invention to provide a compound which overcomes at least some of the problems with the catalysts of the prior art.

SUMMARY OF THE INVENTION

According to the invention we provide a method of manufacturing a polyurethane composition by mixing together a composition containing a polyol, a polyisocyanate compound and a catalyst and allowing the mixture to cure to form a polyurethane, characterised in that the catalyst is a compound of Ti, Zr, Hf, Al, Fe, Bi or Sn which is hydrolytically stable.

According to a second aspect of the invention, we provide a method of manufacturing a polyurethane composition by mixing together a composition containing a polyol, a polyisocyanate compound and a catalyst and allowing the mixture to cure to form a polyurethane, characterised in that the catalyst is a complex of a metal selected from Ti, Zr, Hf, Al, Fe, Bi or Sn and a multidentate organic ligand having:
a) a number of anionic donor sites=x;
b) a number of neutral donor sites, capable of forming a co-ordinate bond with the metal, =y;
c) where x+y=from 5 to 8;
d) x is from 2 to 4;
e) the ligand molecule is of a size and conformation to enable each of the anionic donor sites and neutral donor sites to form a bond with the same metal atom, and
and wherein the complex is neutral.

Preferably the ligand-forming molecule has a structure in which each donor site is in a $\beta$ or a $\gamma$ position relative to at least one other donor site. In preferred compounds, the ligand—metal complex has a structure in which the number of metal—ligand bonds is six.

The anionic donor sites preferably comprise —O$^-$ or —N$^-$—. The neutral donor sites preferably comprise N, O or P atoms, more preferably, N or O atoms.

Figure 1:
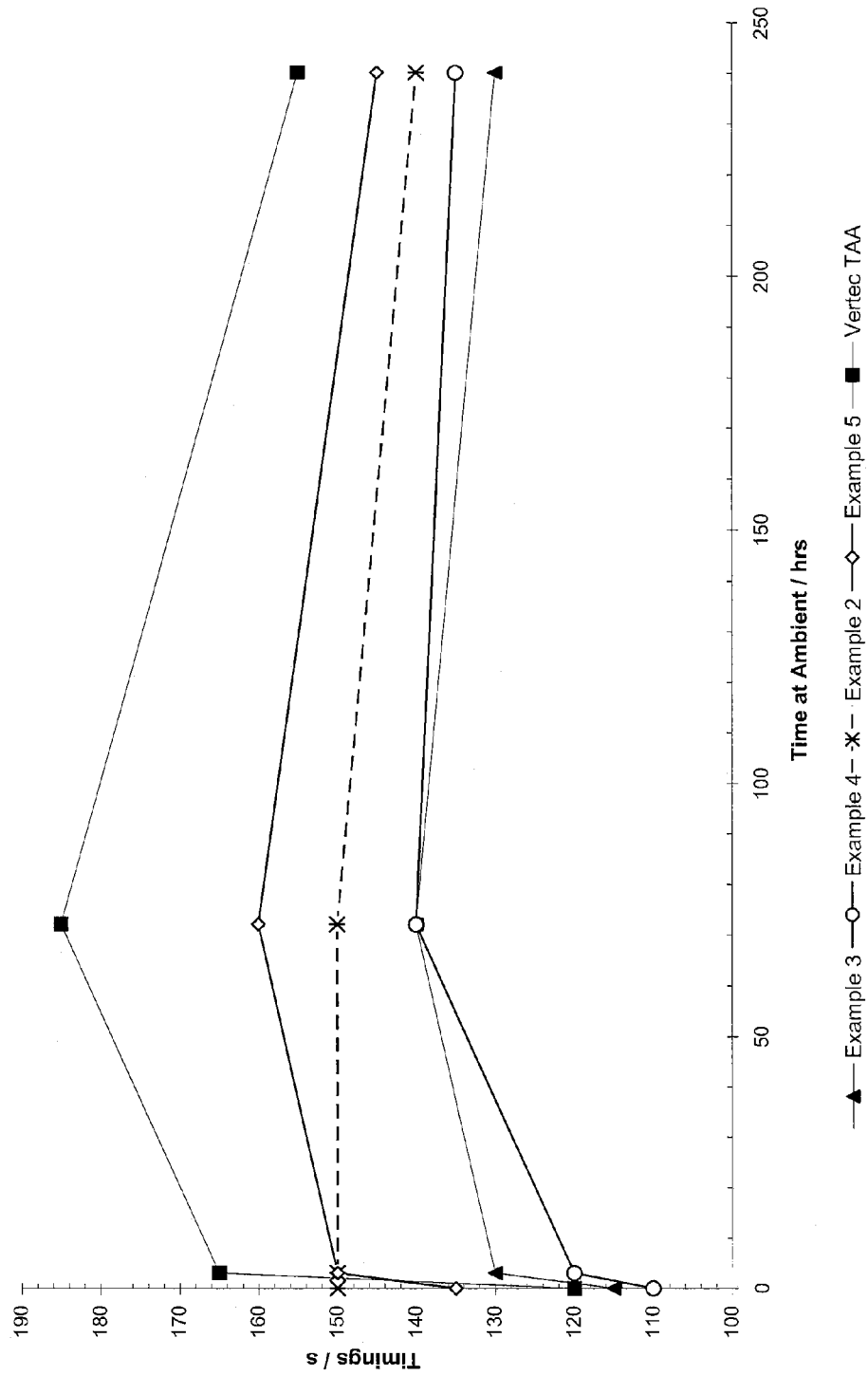
FIG. 1 shows plots of gel time for several catalysts as a function of storage time of mixed polyol plus catalyst.

In a preferred embodiment of the invention the catalyst comprises a metal-organic compound which is the reaction product of a compound of a metal selected from Ti, Zr, Hf, Al, Fe, Bi and Sn with a ligand-forming compound having the following formula:

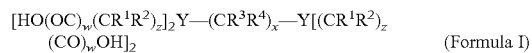
(Formula I)

in which:
Y is selected from P and N, but is very preferably N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3
each w is independently 0 or 1.

In a further embodiment of the invention the catalyst comprises a metal-organic compound has the formula of Formula II:

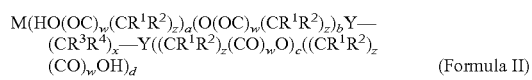
(Formula II)

in which:

M is a metal atom selected from Ti, Zr, Hf, Al, Fe and Sn

Y is selected from P and N, but is very preferably N;

each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4;

x represents the least number of C atoms between the Y atoms and is 2 or 3 each w is independently 0 or 1.

The metal M is selected from titanium, zirconium, hafnium, aluminium, iron (III), bismuth and tin(IV). Particularly preferred metals include titanium and zirconium, especially titanium.

Y represents oxygen, nitrogen or phosphorus but is most preferably a nitrogen atom. The Y atom is capable of forming a co-ordinate bond with the metal to stabilise the complex. Without wishing to be bound by theory, it is believed that the electronic structure of N is particularly susceptible to the formation of such bonds in the complex.

Each $R^1$ and $R^2$, may be the same as or different from each other $R^1$ and $R^2$. This means also that in Formulas I and II, each of the $(CR^1R^2)_z$ moieties may be the same or different. They may be selected from H, alkyl, aryl, substituted alkyl or substituted aryl. When $R^1$ and/or $R^2$ is an alkyl or substituted alkyl, the alkyl group preferably contains from 1 to 12, more preferably from 1 to 8 carbon atoms and may be straight or branched. When $R^1$ and/or $R^2$ is an aryl or substituted aryl group then it is preferably a phenyl group, or a substituted phenyl. The group $-(CR^1R^2)_z-$ may form a part of a larger structure, such as an aryl or cycloalkyl ring for example and in such cases $R^1$ and $R^2$ may be linked to each other or to another $CR^1R^2$ moiety when z>1. In preferred embodiments, each one of $R^1$ and $R^2$ is a hydrogen atom or a methyl group. In a preferred compound each one of $R^1$ and $R^2$ is a hydrogen atom.

$R^3$ and $R^4$ may be the same as or different from each other. They may be selected from H, alkyl, aryl, substituted alkyl or substituted aryl and may be selected from the same groups described in relation to $R^1$ and $R^2$. $R^3$ and $R^4$ may be the same as or different from $R^1$ and/or $R^2$. $-(CR^3R^4)_x-$ is a bridging group between the two Y atoms. X represents the number of C atoms between the two Y atoms and is preferably 2 or 3 so that when the Y atoms each form a co-ordinate bond the metal, Y atoms and bridging group $-(CR^3R^4)_x-$ together form a 5- or 6-membered ring. The bridging group $-(CR^3R^4)_x-$ may form a part of a larger structure, such as an aryl or cycloalkyl ring for example and in such cases $R^3$ and $R^4$ may be linked to each other or to another $CR^3R^4$ moiety when x>1. In one preferred embodiment each one of $R^3$ and $R^4$ is a hydrogen atom or a methyl group, and is more preferably a hydrogen atom. In a preferred compound each one of $R^3$ and $R^4$ is a hydrogen atom.

By appropriate selection of $R^1$, $R^2$, $R^3$ and $R^4$, the compound may be chiral at one or more of the $CR^1R^2$ or $CR^3R^4$ carbon atoms.

When w=0, then $(HO(OC)_w(CR^1R^2)_z$ is an alcohol group and the ligand forming compound has a reactive hydroxyl group which can form a metal-oxygen-carbon linkage. When w=1, then $(HO(OC)_w(CR^1R^2)_z$ is a carboxylic acid group which can react with the metal to form a carboxylate linkage. The compound may have a combination of carboxylic acid groups and hydroxyl functional groups, i.e. each w in Formula I and II may be the same but need not be.

Each z is 1, 2, 3 or 4 and may be the same as of different from each other z. When w=0 then z is preferably at least 2 and more preferably z is 2 or 3 and when w=1 then z is preferably 1 or 2, in each case such that the metal, $-O(CR^1R^2)_z$ moiety and the Y atom may together form a 5- or 6-membered ring in the metal-organic compound.

The metal organic compound of the invention is a chelate formed by the reaction of the compound of Formula I with a metal compound. When metal M has a valency of 4, any or all of the four hydroxyl or carboxylic acid functional groups may react with the metal to form a metal oxygen covalent bond. In this case, in Formula II, b and c are each 2 and d and a are both 0. When the valency of M is less than 4, not all of the functional groups can react at any one time and therefore there may be unreacted hydroxyl groups present in the chelate. These hydroxyl groups may, however, form co-ordinate bonds with metal M and therefore participate in stabilising the chelate. When M is a trivalent metal, in Formula II, a=1, b=1, c=2 and d=0.

A preferred ligand-forming compound comprises (HO$(CH_2)_2)_2$N—$(CH_2)_2$—N$((CH_2)_2OH)_2$ i.e. N,N,N',N'-tetrakis(2-hydroxyethyl)ethylenediamine, which may be known as and designated herein as THEED. In one preferred embodiment, the metal organic compound comprises N,N,N',N'-tetrakis(2-oxyethyl)ethylenediamine titanium Ti(TOEED). This is believed to be a new compound. This compound is very stable to hydrolysis and so may be used as a catalyst for reactions in which water is present. A second preferred ligand-forming compound comprises (HOCH($CH_3$)$CH_2$)$_2$N—$(CH_2)_2$—N$(CH_2CH(CH_3)OH)_2$ i.e. N,N,N',N'-tetrakis(2-hydroxypropyl)ethylenediamine, which may be known as and designated herein as THPED. A preferred catalyst formed from THPED is N,N,N'N'-tetrakis-(2-oxypropyl)ethylenediamine titanium (which may be known and designated herein as Ti(TOPED)). Another preferred ligand-forming compound is ethylenediaminetetra(acetic acid) (EDTA).

In one embodiment of the invention we provide a method of manufacturing a polyurethane composition by mixing together a composition containing a polyol, a polyisocyanate compound and a catalyst comprising a hydrated compound having the empirical formula M(HO(CR$^1$R$^2$)$_z$)$_a$(O(CR$^1$R$^2$)$_z$)$_b$Y—(CR$^3$R$^4$)$_x$—Y((CR$^1$R$^2$)$_z$O)$_c$((CR$^1$R$^2$)$_z$OH)$_d$.nR$^5$OH in which a, b, c, d, x, z, all $R^{1-4}$ and Y are as described above in Formula II. The value of n depends on the metal and its coordination number. n=1 when M is a metal such as titanium or tin (IV), having an oxidation state of 4 and are believed to be 7-coordinate in the compounds described. When M is a metal such as zirconium or hafnium, having an oxidation state of 4 and a coordination number of 8, then n=1 or 2. $R^5$ is hydrogen, an alkyl group or a hydroxy-functionalised alkyl group so that $R^5$OH represents water, an alkyl alcohol or a diol or polyol. Preferred hydrated compounds include N,N,N',N'-tetrakis(2-oxyethyl)ethylenediamine metal hydrate, and N,N,N',N'-tetrakis(2-oxypropyl)ethylenediamine metal hydrate where the metal is selected from titanium, zirconium, hafnium, aluminium, iron (III) and tin(IV). The hydrated forms of the compound are particularly stable to hydrolysis and may be stored in contact with water for extended periods of time without significant loss of catalytic activity. The hydrated compound is formed when the non-hydrated compound is mixed with water. It is therefore also likely to be formed in situ when the compound is present in a reaction mixture with water. Therefore when the catalyst comprises a non-hydrated form of the Ti(TOEED) and it is stored in a polyol composition containing water, a stable hydrate, which is resistant to further hydrolysis, may form in situ. When $R^5$OH is an alcohol (or a polyol, including a diol)

then the alcohol coordinates to the metal, stabilising the complex. When water is present, the water-stabilised complex and the alcohol-stabilised complex exist in equilibrium.

The metal-organic compound may be prepared by mixing together a metal compound with the ligand-forming compound(s) with stirring. The reactants may be added in any order. Heating or cooling may be provided if required. When the metal-organic compound contains more than one type of ligand, the ligands may be mixed together in the required proportions and then a metal compound, such as a metal alkoxide, may be added to the mixture of ligands. Alternatively, when more than one type of ligand is required, a metal chelate may be formed between the metal and a first ligand and then a second ligand may be added to the chelate to form a mixed ligand metal chelate. When the metal organic compound comprises N,N,N',N'-tetrakis(2-oxyethyl)ethylenediamine titanium (i.e. Ti(TOEED)) formed by the addition of the ligand compound to a titanium alkoxide, the reaction becomes quite hot. The co-product(s) from the reaction of the ligand-forming compound with the metal compound may be removed from the reaction mixture by suitable means such as by distillation, derivitisation, or other separation means depending on the nature of the product. The co-product is e.g. a hydrogen halide or an alcohol when a metal halide or alkoxide is used as the starting metal compound. The co-product may alternatively be retained in the final product if desired. The reaction may take place in the presence of a suitable solvent if required.

The metal compound is capable of reacting with at least one of the hydroxyl groups present in the ligand-forming compound to form a metal-oxygen bond. Suitable metal compounds include metal halides, metal alkoxides, metal haloalkoxides, metal carboxylates and mixtures of these compounds. Typical alkoxides have the general formula $M(OR)_x$ in which M is Ti, Zr, Hf, Sn, Al or Fe, x is the oxidation state of the metal, i.e. 3 or 4, and R is a substituted or unsubstituted, cyclic or linear, alkyl, alkenyl, aryl or alkyl-aryl group or mixtures thereof. Preferably, R contains up to 8 carbon atoms and, more preferably, up to 6 carbon atoms. Generally, all OR groups are identical but alkoxides derived from a mixture of alcohols can be used and mixtures of alkoxides can be employed when more than one metal is present in the complex. When the metal is titanium, preferred titanium compounds include titanium alkoxides having a general formula $Ti(OR)_4$ in which R is an alkyl group, preferably having from 1 to 8 carbon atoms and each R group may be the same as or different from the other R groups. Particularly suitable metal compounds include titanium tetrachloride, titanium tetra-isopropoxide, titanium tetra-n-propoxide, titanium tetra-n-butoxide, titanium tetraethoxide (tetraethyl titanate), zirconium n-propoxide, zirconium butoxide, hafnium butoxide, tin isopropoxide, tin butoxide, tin tetrachloride and tin tetrabromide, aluminium sec-butoxide, aluminium trichloride, iron (III) chloride, aluminium trimethoxide, bismuth octoate, iron trimethoxide, aluminium triethoxide, iron triethoxide, aluminium tri-isopropoxide, iron tri-isopropoxide, aluminium tri-n-propoxide, iron tri-n-propoxide, aluminium tritertiarybutoxide, iron tritertiarybutoxide, and iron tri-sec-butoxide.

The metal-organic compound may include further chelating ligands. Such a compound may have the empirical formula: $M(HO(CR^1R^2)_z)_a(O(CR^1R^2)_z)_bY-(CR^3R^4)_x-Y((CR^1R^2)_zO)_c((CR^1R^2)_zOH)_d(L)_n$ in which M, a, b, c, d, x, z, all $R^{1-4}$ and Y are as described above in Formula II. The value of n depends on the metal and its coordination number. n=1 when M is a metal such as titanium or tin (IV), having an oxidation state of 4 and are believed to be 7-coordinate in the compounds described. When M is a metal such as zirconium or hafnium, having an oxidation state of 4 and a coordination number of 8, then n=1 or 2. The further chelating ligand L is a monodentate or bidentate ligand and is preferably derived from one or more compounds including beta-diketones such as acetylacetone (pentanedione) and t-butyl acetylacetone (2,2,6,6-tetramethyl-3,5-heptanedione); beta-ketoesters such as ethylacetoacetate and other alkylacetoacetates; beta-ketoamides such as N,N-diethylacetoacetamide; acid phosphates and phosphate esters such as mono and/or dialkyl acid phosphates; organic sulphonic acids, phosphoric acid, organic carboxylic acids such as isostearic acid, salicylic acid, phenols, alpha-hydroxyacids such as citric acid, lactic acid, mandelic acid etc. Particularly preferred compounds of this type include:

Ti(N,N,N',N'-tetrakis(2-oxyalkyl)ethylenediamine)
Ti(N,N,N',N'-(2-oxyalkyl)$_3$(2-hydroxyalkyl)ethylenediamine)(pentanedionato),
Ti(N,N,N',N'-(2-oxyalkyl)$_3$(2-hydroxyalkyl)ethylenediamine)(ethylacetoacetato),
Ti(N,N,N',N'-(2-oxyalkyl)$_3$(2-hydroxyalkyl)ethylenediamine)(N,N-diethylacetoacetamido)
Ti(N,N,N',N'-(2-oxyalkyl)$_3$(2-hydroxyalkyl)ethylenediamine)(isostearate)
Ti(N,N,N',N'-(2-oxyalkyl)$_3$(2-hydroxyalkyl)ethylenediamine)(salicylate)
Ti(N,N,N',N'-(2-oxyalkyl)$_3$(2-hydroxyalkyl)ethylenediamine)(mandelate)
Ti(N,N,N',N'-(2-oxyalkyl)$_3$(2-hydroxyalkyl)ethylenediamine)(2,2,6,6-tetramethyl-3,5-heptanedionato) where oxyalkyl may be oxyethyl, oxypropyl or oxybutyl, and the zirconium analogues of these compounds. Additional quantities of the further chelating ligand may be present in the composition.

In a particular embodiment a catalyst composition comprises a metal-organic chelate compound as hereinbefore described and a co-catalyst which is selected to be an effective trimerisation catalyst. The co-catalyst is preferably an organic nitrogen-containing compound selected from quaternary ammonium compounds and amines. Although organic amines are well known as catalysts for curing polyurethane compositions, it is an important feature of the present invention that the co-catalyst is effective for the reaction of an isocyanate group with another isocyanate group or a urethane group- to form a trimer, allophanate or biuret moiety, which enables the catalyst composition to form cross-links in the polyurethane material in order to build the required physical properties to produce a strong polyurethane product. Trimerisation is the result of the reaction of polyisocyanates and isocyanate ended-polyurethane molecules with other isocyanate groups to form stable trimers, known as polyisocyanurates. The co-catalyst, when mixed with an aromatic isocyanate, is preferably capable of producing trimer at temperatures below 80° C. Suitable co-catalysts include amines such as N,N',N"-tris(N,N'-(dialkylamino)alkyl) hexahydro-s-triazines such as 1,3,5 tris(3-(dimethylamino)propyl)hexahydro-s-triazine available under the trade names: POLYCAT™ 41, NIAX™ C-41, JEFFCAT™ TR41, LUPRAGEN™ N600, JEFFCAT™ TR90 and TOYOCAT™-TRC; 1,3,5-tris(N,N-dimethyl-2-aminoethyl)-s-hexahydrotriazine, 1,3,5-tris(N,N-dimethyl-2-aminopropyl)-s-hexahydrotriazine, 1,3,5-tris(N,N-diethyl-2-aminoethyl)-s-hexahydrotriazine; 1,3,5-tris(N,N-diethyl-3-aminopropyl)-s-hexahydrotriazine, 1,3,5-tris(N,N-dipropyl-2-aminoethyl)-s-hexahydrotriazine,
-pentamethyldiethylenetriamine e.g. as sold as POLYCAT™ 5, POLYCAT™ 9, DABCO™ F02051, POLYCAT™ SA-1, POLYCAT™ DBU, the proprietary blend of trimerisation amines sold as DABCO TMR-13, N-methyldicyclohexylamine sold under the trade name of POLYCAT™ 12, N,N-dimethylethanolamine, N,N-dimethylcyclohexylamine, N,N-dimethylbenzylamine, N,N,N',N'-tetramethyl-1,3-butanediamine, N,N,N',N'-tetramethylpropanediamine, N-methylmorpholine, N-ethylmorpholine, triethylene diamines, mono(dialkylaminoalkyl)phenols, dialkylaminoalkoxyalcohols such as dimethylaminoethoxyethanol (sold as DABCO DMAEE, JEFFCAT™ ZR-70), and 2,4,6 tris(alkylaminoalkyl)phenols such as 2,4,6-tris(dimethylaminomethyl) phenol (e.g. DABCO™ TMR-30, JEFFCAT™ TR30). The N,N',N"-tris(N,N'-(dialkylamino)alkyl)hexahydro-s-triazines are preferred trimerisation catalysts, in particular 1,3,5-tris(N,N-dimethyl-3-aminopropyl)-s-hexahydrotriazine which can also be designated as 1,3,5-tris(3-dimethylaminopropyl)-s-hexahydrotriazine.

Other suitable trimerisation catalysts include alkali metal or, more preferably, quaternary ammonium salts of oxygen-containing acids, especially carboxylic acids, sulphonic acids and phosphorus-containing acids such as phosphoric, phosphonic and phosphinic acids and their alkyl esters. The carboxylic acids, sulphonic acids and phosphorus-containing acids may optionally contain additional ester or amide functionality as described in U.S. Pat. No. 4,540,781. Suitable examples of trimerisation catalysts comprising quaternary ammonium salts include DABCO™ TMR, hydroxyalkyltrialkylammonium carboxylates, e.g. 2-hydroxypropyltrimethylammonium octylate, 2-hydroxypropyltrimethylammonium formate, DABCO™ TMR-2, DABCO™ TMR-3, hydroxyalkyl ammonium formate, DABCO™ TMR-5, CURITHANE™ 52, ADDOCAT™ 1594, methyltriethylammonium octylate, methyltriethylammonium formate, N-8-methyl-1,8-diazabicyclo[5,4,0]-7-undecene octylate. Other compounds may also be suitable, for example, an N,N-dialkylacetoacetamide, e.g. N,N-diethylacetoacetamide, or a 2,3-dialkyltetrahydropyrimidine such as 2,3-dimethyltetrahydropyrimidine. Sodium glycinate and other alkali metal compounds may also be suitable. DABCO, CURITHANE and POLYCAT are trademarks of Air Products Inc, JEFFCAT is a trademark of Huntsman Inc, ADDOCAT is a trademark of the RheinChemie Group, TOYOCAT is a trademark of the Tosoh Corporation.

The relative amounts of the metal-organic compound and the co-catalyst (when present) in the catalyst composition should be such as to provide an optimised balance of urethane formation (i.e. gelling activity) and cross-linking so that the proportions used depend upon the nature of the catalyst compounds used, the polyol and isocyanate and the properties required from the finished product. Typically the amounts of metal-organic compound and the co-catalyst in the catalyst composition are from 1 to 20 parts by weight (pbw) of the metal-organic compound and from 1 to 20 pbw of the co-catalyst. Preferably the relative amount of metal-organic compound to cocatalyst is in the range 1:10 to 2:1 (metal-organic compound: cocatalyst expressed as weight ratios). The metal-organic compound and the co-catalyst are preferably mixed to form a mixed catalyst composition, which is preferably in the liquid phase. Alternatively, but less preferably, the metal-organic compound and the co-catalyst are added to one of the polyurethane reactants (i.e. the polyol composition or the polyisocyanate compound) separately.

The stability of the metal chelate compounds in water makes them suitable for use in compositions for the manufacture of polyurethanes in which water is present. For example, the catalyst may be incorporated in a polyol composition containing significant quantities of added water, especially when the composition has been prepared for use in making foams or water-based coatings. The use of some additives in polyurethane formulations, e.g. fillers such as calcium carbonate, often incorporates water into the composition.

Compositions for use in making polyurethane materials which contain the catalyst described above are also within the scope of this invention. Such compositions comprise at least one of a polyol and a polyisocyanate, the catalyst and optionally at least one other additive. The polyol, polyisocyanate and additives are further discussed below, are not intended to be limiting and are well known to any person skilled in formulating polyurethane compositions.

The catalysts used in the invention may be supplied neat (particularly when the composition is, itself a liquid) or supplied as a formulated composition containing a solvent or diluent, which may be present in quantities representing up to 90% of the weight of the total catalyst composition (i.e. including the diluent), more preferably up to 50% by weight. The solvent or diluent may comprise water, an alcohol, diol or polyol, another protic solvent or a glycerol-based oil, especially naturally derived oils such as castor oil, rape-seed oil etc. Any other diluent which is miscible with the polyol, polyisocyanate or prepolymer used in the polyurethane formulation may be used. In some formulations, it is preferred to use as a diluent a liquid component which is already present in or which is compatible with the polyurethane reaction components, such as a diol or polyol which may function as a chain extender e.g. 1,4-butane diol or diethylene glycol. Preferred diluents include 1,3-propanediol, 1,4-butanediol, diethylene glycol, glycerol, and natural oils such as castor oil and rape-seed oil.

The process of the invention is comprises the reaction between a hydroxyl-functionalised molecule, such as a polyol, and an isocyanate-functionalised molecule, such as a polyisocyanate to form a polyurethane in the form of an elastomer, an adhesive, a foam, a thermoplastic mouldable material, a coating or any other useful physical form. This reaction forms the basis of many commercially available two-component polyurethane systems.

The polyol component may be any suitable for the manufacture of polyurethanes and includes polyester-polyols, polyester-amide polyols, polyether-polyols, polythioether-polyols, polycarbonate polyols, polyacetal polyols, polyolefin polyols polysiloxane polyols, dispersions or solutions of addition or condensation polymers in polyols of the types described above, often referred to as "polymeric" polyols. A very wide variety of polyols has been described in the prior art and is well known to the formulator of polyurethane materials.

Typically, a mixture of polyols is used to manufacture polyurethane having particular physical properties. The polyol or polyols is selected to have a molecular weight, backbone type and hydroxy functionality which is tailored to the requirements of the formulator. The polyol composition may include a chain extender, which is often a relatively short-chain diol such as 1,4-butane diol or diethylene glycol or a low molecular weight polyethylene glycol. Alternative chain extenders in commercial use, such as diamines, e.g. MOCA (4,4-methylene bis(2-chloroaniline)) may also be used.

The isocyanate compositions used for polyurethane manufacture suitable for use with the catalysts of the present invention may be any organic polyisocyanate compound or mixture of organic polyisocyanate compounds which are commercially useful for the purpose. Preferably the polyisocyanate is liquid at room temperature. Suitable organic polyisocyanates include diisocyanates, particularly aromatic diisocyanates, and isocyanates of higher functionality. Examples of suitable organic polyisocyanates include aliphatic isocyanates such as hexamethylene diisocyanate and isophorone diisocyanate; and aromatic isocyanates such as m- and p-phenylene diisocyanate, tolylene-2,4- and tolylene-2,6-diisocyanate, diphenylmethane-4,4'-diisocyanate, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyldiphenylmethane-4,4'-diisocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane and triisocyanates such as 2,4,6-triisocyanatotoluene and 2,4,4-tri-isocyanatodiphenylether.

Modified polyisocyanates containing isocyanurate, carbodiimide or uretonimine groups may be used. The polyisocyanate may also be an isocyanate-ended prepolymer made by reacting an excess of a diisocyanate or higher functionality polyisocyanate with a polyol for example a polyether polyol or a polyester polyol. The use of prepolymers is common in commercially available polyurethane systems. In these cases, polyols may already be incorporated in the isocyanate or prepolymer whilst further components such as chain extenders, polyols etc may be mixed with the isocyanate prepolymer mixture before polymerisation.

Mixtures of isocyanates may be used in conjunction with the organometallic composition of the invention, for example a mixture of tolylene diisocyanate isomers such as the commercially available mixtures of 2,4- and 2,6-isomers. A mixture of di- and higher polyisocyanates, such as trimers (isocyanurates) or pre-polymers, may also be used. Polyisocyanate mixtures may optionally contain monofunctional isocyanates such as p-ethyl phenylisocyanate.

The catalyst is typically added to the polyol prior to mixing together the polyol component with the isocyanate component to form the polyurethane. The mixture of the catalyst and the polyol component may be stored after mixing and prior to use to form a polyurethane.

A composition containing a catalyst composition of the present invention and a polyol and compounds reactive therewith may further comprise conventional additives such as chain modifiers, diluents, flame retardants, blowing agents, release agents, water, coupling agents, lignocellulosic preserving agents, fungicides, waxes, sizing agents, fillers, colourants, impact modifiers, surfactants, thixotropic agents, flame retardants, plasticisers, and other binders. Additional catalysts may also be present such as blowing catalysts and secondary catalysts, e.g. amines. The selection of these and other ingredients for inclusion in a formulation for a polyurethane composition is well known to the skilled person and may be selected for the particular purpose. When the mixture has been allowed to cure it may be further conditioned to allow for post-cure. Typically this occurs when the polyurethane article, coating etc has hardened to a state in which it may be handled, demoulded etc and then it may be held at elevated temperature, e.g. by placing in an oven, to develop or enhance the full cured properties of the article.

The process and compositions of the present invention are useful for the manufacture of polyurethane foams, flexible or rigid articles, coatings, adhesives, elastomers, sealants, thermoplastic polyurethanes, and binders. The catalysts of the present invention may also be useful in preparing polyurethane prepolymers, i.e. urethane polymers of relatively low molecular weight which are supplied to end-users for curing into polyurethane articles or compositions of higher molecular weight.

The catalysts are typically present in the isocyanate and/or polyol mixture to give a concentration in the range $1 \times 10^{-4}$ to 10% by weight, preferably up to about 2% by weight based upon the weight of the total reaction system, i.e. the total weight of the polyisocyanate and polyol components.

EXAMPLES

The invention will be further described in the following examples.

Example 1

Preparation of Ti(TOEED)

236 g (1 mole) of N,N,N',N'-tetrakis(2-hydroxyethyl)ethylenediamine (THEED) (from Sigma-Aldrich/Fluka) was added to 284 g (1 mole) of tetra(isopropoxy)titanium (VERTEC™ TIPT, from Johnson Matthey Catalysts) slowly and with stirring, to give a clear yellow solution. The isopropanol produced in the reaction was removed by rotary evaporation under reduced pressure to yield a pale yellow powder (280 g) of N,N,N',N'-tetrakis(2-oxyethyl)ethylenediamine titanium (Ti(TOEED)).

The compound was dissolved in water to form a 10% w/w aqueous solution. The solution was boiled for one hour and then the water was removed by evaporation. The resulting pale yellow powder was found to be the same compound as the starting material, showing that the compound was stable to hydrolysis under the conditions used. The yellow powder was recrystallised from chloroform and analysed using $^1$H-NMR, elemental analysis and a crystal structure determined by X-ray crystallography.

The NMR analysis yielded the following chemical shift data (relative to tetramethyl silane (TMS), where m indicates a multiplet, which is consistent with the presence of N,N,N',N'-tetrakis(2-oxyethyl)ethylenediamine titanium:

$^1$H NMR (400 MHz); 4.86-4.72 (2H, m), 4.72-4.60 (2H, m), 4.60-4.52 (1H, m), 4.52-4.43 (1H, m), 4.16-4.08 (1H, m), 4.08-4.01 (1H, m), 3.64-3.52 (2H, m), 3.43-3.31 (2H, m), 3.31-3.16 (2H, m), 3.12-3.01 (1H, m), 2.97-2.71 (5H, m).

The elemental analysis yielded the following data:

Found: C, 42.43; H, 7.19; N, 9.79%.

Theoretical for [Ti(THEED)]$_2$: C, 42.87; H, 7.20; N, 10.00%.

Ti Content (wt %): Found: 16.98%, Theoretical for [Ti(TOEED)]$_2$: 17.08%

Figure 4:
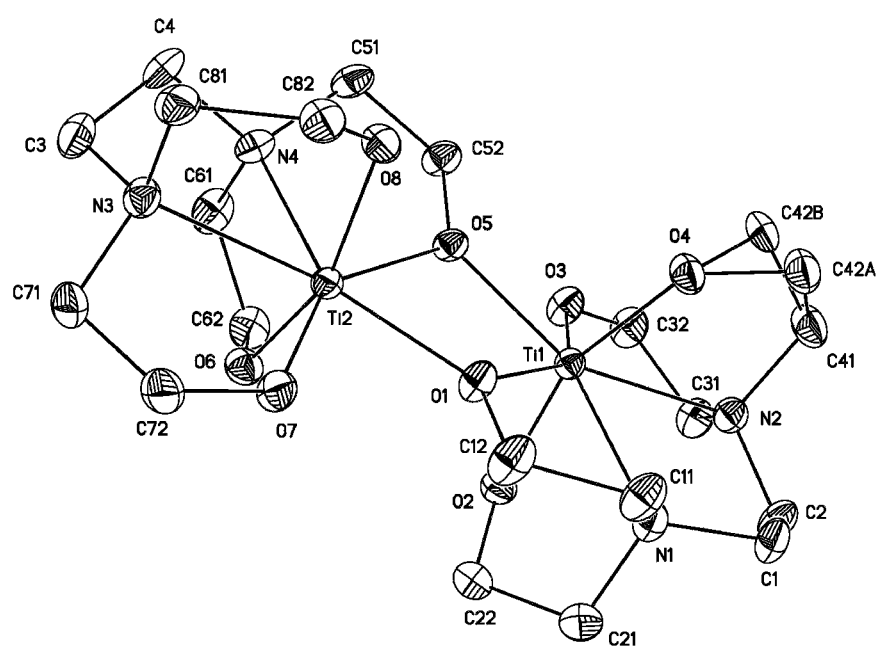
FIG. 4 shows a crystal structure obtained for N,N,N',N'-tetrakis(2-oxyethyl)ethylenediamine titanium.

The crystal structure is presented in FIG. 4. The structure appears to be dimeric, having two Ti centres bridged by two oxygen atoms, designated O1 and O5 in the diagram.

Example 2

Ti(TOEED) (0.513 g) was dissolved in deionised water (1.212 g) and the suspension was stirred for 30 minutes at 60° C. until all of the solid had dissolved.

Example 3

Ti(TOEED) (0.512 g) was dissolved in diethyleneglycol (1.235 g) and the suspension was stirred for 60 minutes at 105° C. until all of the solid had dissolved.

Example 4

Ti(TOEED) (0.520 g) was dissolved in denatured ethanol (1.222 g) and the suspension was stirred for 30 minutes at 40° C. until all of the solid had dissolved.

Example 5

Tetra(isopropoxy)titanium (1 mole, 284 g) was added to a rotary evaporator flask. To this was slowly added 2 moles of triethanolamine (TEA)(298 g) keeping the temperature below 50° C. and the solution (Ti(TEA)(IPA)$_2$+2IPA) was mixed for 30 minutes at 40° C.

Example 6

Use of Catalyst to Prepare Polyurethane Foam

A polyol composition was made up as shown in Table 1. The amount of water added to the polyol composition was sufficient to bring the total amount of water used (including any contained in the catalyst preparation) to 2.7 parts.

The polyol composition was used to make a polyurethane foam, either immediately after its preparation or after a period of time stored at 25° C. The foam was prepared by mixing the polyol composition with 102.3 parts of a commercially available polyisocyanate in a 500 ml cup. The mixture rises due to the action of the blowing catalyst and sets into a foam as the gelling catalyst promotes reaction of the polyol with the isocyanate to form a polyurethane. The reaction is studied by measuring the time taken for the foam to reach the top of the cup (top of cup time), the gel time and the time at which the foam stopped rising (end of rise time).

Figure 2:
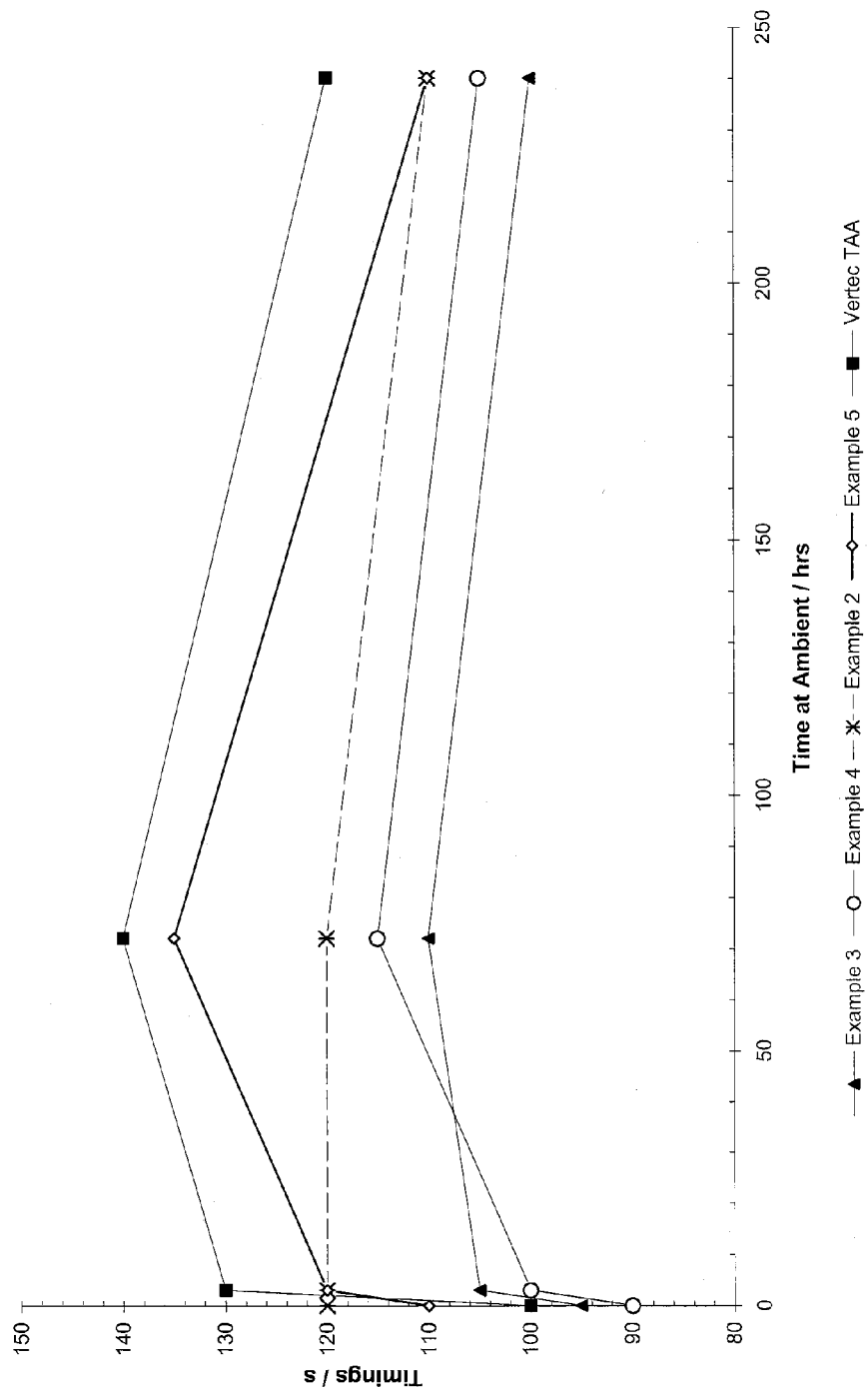
FIG. 2 shows plots of top of cup time for several catalysts as a function of storage time of mixed polyol plus catalyst.
Figure 3:
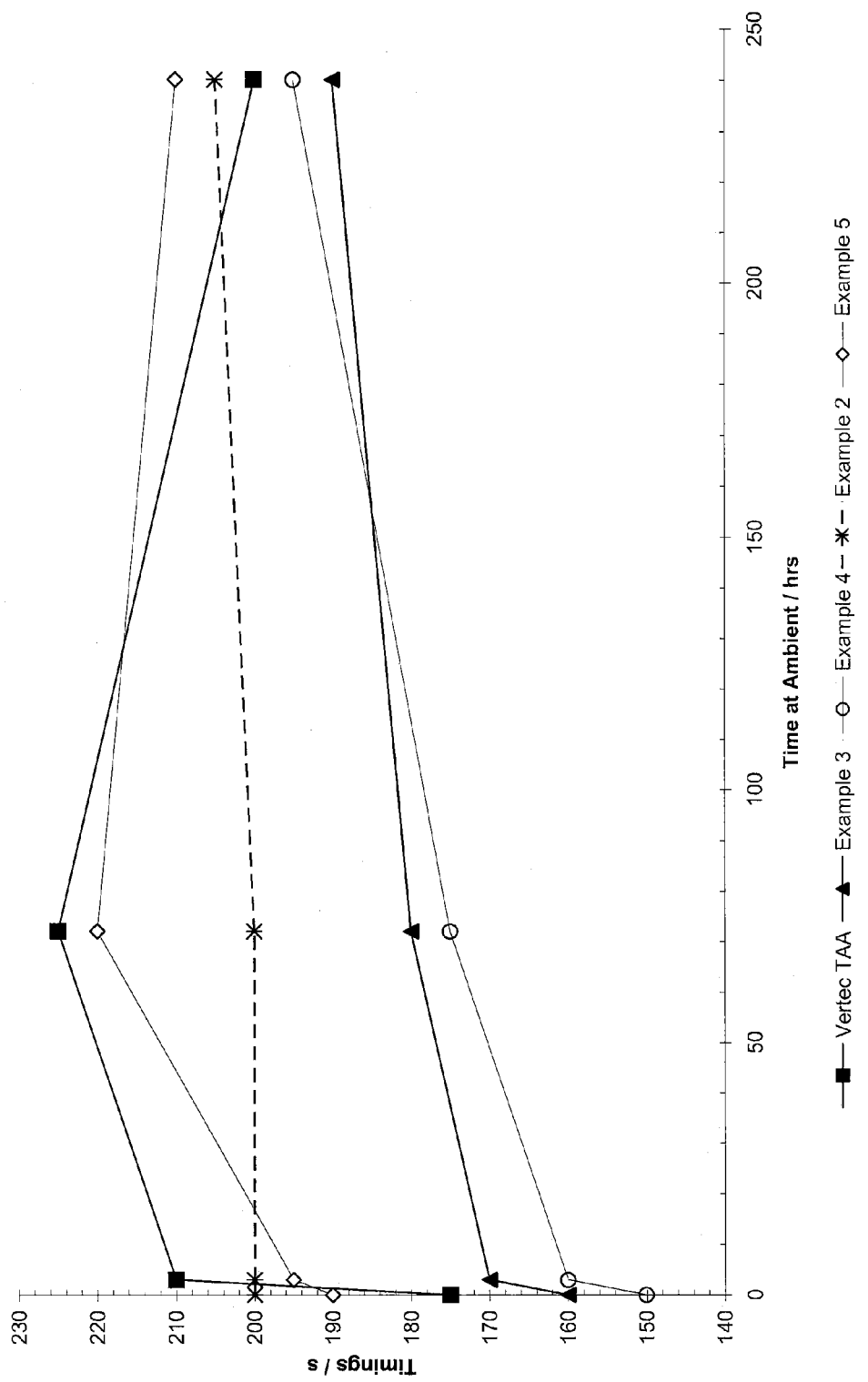
FIG. 3 shows plots of end of rise time for several catalysts as a function of storage time of mixed polyol plus catalyst.

The results are shown graphically in FIGS. 1-3. In each plot the y-axis shows the gel time, top of cup time or end of rise time as appropriate and longer times indicate a less reactive catalyst. The x-axis shows the time in hours for which the polyol composition containing the catalyst was stored before mixing with the polyisocyanate. It should be noted that the ambient temperature was not the same during preparation of the foam and the warmer temperature experienced during the test at 240 hours has increased the speed of the reactions. The catalyst of Example 2 shows a very consistent behaviour which is independent of the storage time. This indicates that the catalyst is hydrolytically stable and so it may be used in compositions which require a relatively long shelf-life. By contrast, the VERTEC TAA titanium acetylacetonate catalyst loses activity very rapidly and continues to become less active on storage in the polyol composition.

TABLE 1

|  | Parts by weight |  |  |  |
| --- | --- | --- | --- | --- |
| Amine/sucrose polyol | 94.6 |  |  |  |
| Dimethylethylamine (DMEA) (blowing catalyst) | 1.0 |  |  |  |
| Silicon foam stabiliser | 1.7 |  |  |  |
| Total water | 2.7 |  |  |  |
| Catalyst (Example 2) | 0.26 |  |  |  |
| Catalyst (Example 3) |  | 0.26 |  |  |
| Catalyst (Example 4) |  |  | 0.26 |  |
| Catalyst (Example 5) |  |  |  | 0.35 |
| Catalyst (VERTEC ™ TAA) |  |  |  |  | 0.24 |

Example 7

Tetraisopropyl titanate (VERTEC™ TIPT) was reacted with acetylacetone in the mole ratio 1 TIPT:2 acetylacetone. The reaction was exothermic and the solution turned orange/yellow. To this was added 1 mole of N,N,N',N'-tetra(hydroxypropyl)ethylenediamine and the complex was then heated at 60° C. for 30 minutes and mixed with 1,3 propanediol to a weight ratio 90% propane diol:10% metal complex to form Cat 1. The complex was used as diluted in propanediol to form a polyurethane elastomer either alone or together with a cocatalyst. The elastomer was made using the following recipe.

(a) A polyol composition was made up according to the recipe in Table 2 and allowed to equilibrate for 24 hours.

(b) Prepolymer Synthesis

An isocyanate-ended prepolymer was made according to the following procedure. 4,4-MDI (1201.7 g) was placed into a reactor and heated until liquid (about 60° C.). 2000 MW polypropylene glycol (793.3 g) was then added into the reactor via a dropping funnel and the heat maintained at 60° C. The mixture was heated until the exotherm occurred and then heated to 110° C. and maintained at that temperature for three hours to produce a quasi prepolymer: calculated NCO content=18.6%, calculated viscosity=300 cps.

TABLE 2

| OH value | compound | Parts by weight | % (polyol) | Mix temperature ° C. |
| --- | --- | --- | --- | --- |
| 56 | *PPG 56-07 | 47 | 46.26 | 40 |
| 28 | *6 K triol | 47 | 46.26 | 40 |
| 1245 | 1,4-butanediol | 6 | 5.91 | 40 |
| 0 | Molecular sieve | 1.5 | 1.48 | 40 |
| 0 | Silicone anti-foam | 0.1 | 0.10 | 40 |
|  | TOTAL | 101.6 | 100.00 |  |

*product commercially available from Dow Chemical Company.

(c) Polyurethane Elastomer Preparation

A polyurethane elastomer was prepared by reacting the polyol composition described in (a) to the prepolymer described in (b) at a ratio of 101.6 parts by weight of the polyol to 51.98 parts by weight of the prepolymer. To between 20-100 g of the polyol side was added between 0.3-0.7 wt % (based on the weight of polyol+catalyst) of the catalyst composition shown in Table 2 and the mixture was mixed on a centrifugal mixer for 30 seconds. The corresponding amount of prepolymer was then added to the polyol and mixed on a centrifugal mixer for another 30 seconds. The reaction mixture was then degassed under vacuum. A portion of the mixture was poured into a small disk shaped mould on a hot plate at 80° C. and the rest into a 50 ml plastic cup at room temperature (RT). The gel time was recorded as the earliest time that no material is removed when touched with a spatula.

The results are shown in Table 3. The catalyst made in example 7 was used alone or as a mixture with a commercial trimerisation catalyst P41=POLYCAT™ 41 (1,3,5 tris(3-(dimethylamino)propyl)hexahydro-s-triazine) or TMR3=DABCO™ TMR-3 (a hydroxyalkylammonium formate), both available from Air Products. A commercial mercury-containing catalyst, HgT535, was tested as a comparison. The results show that use of Cat 1 alone or in combination with DABCO TMR-3 or POLYCAT 41 is effective in producing polyurethanes having a relatively short gel-time.

TABLE 3

| | Catalyst | wt % in polyol | 80° C. hot plate gel time | RT gel time |
|---|---|---|---|---|
| *A | Hg T535 | 0.7 | 4:00 | 9:00 |
| B | Cat 1 | 0.7 | 4:30 | 14:00 |
| *C | P41 | 0.4 | 4:30 | 20:00 |
| D | 70% Cat 1 + 30% P41 | 0.3 | 4:30 | 10:00 |
| *E | TMR3 | 0.4 | 4:30 | 18:00 |
| F | 70% Cat 1 + 30% TMR3 | 0.3 | 3:40 | 6:00 |

*In the table, A, C and E are not according to the invention and are shown only for comparative purposes.

Example 8

Polyurethane Elastomer

Figure 5:
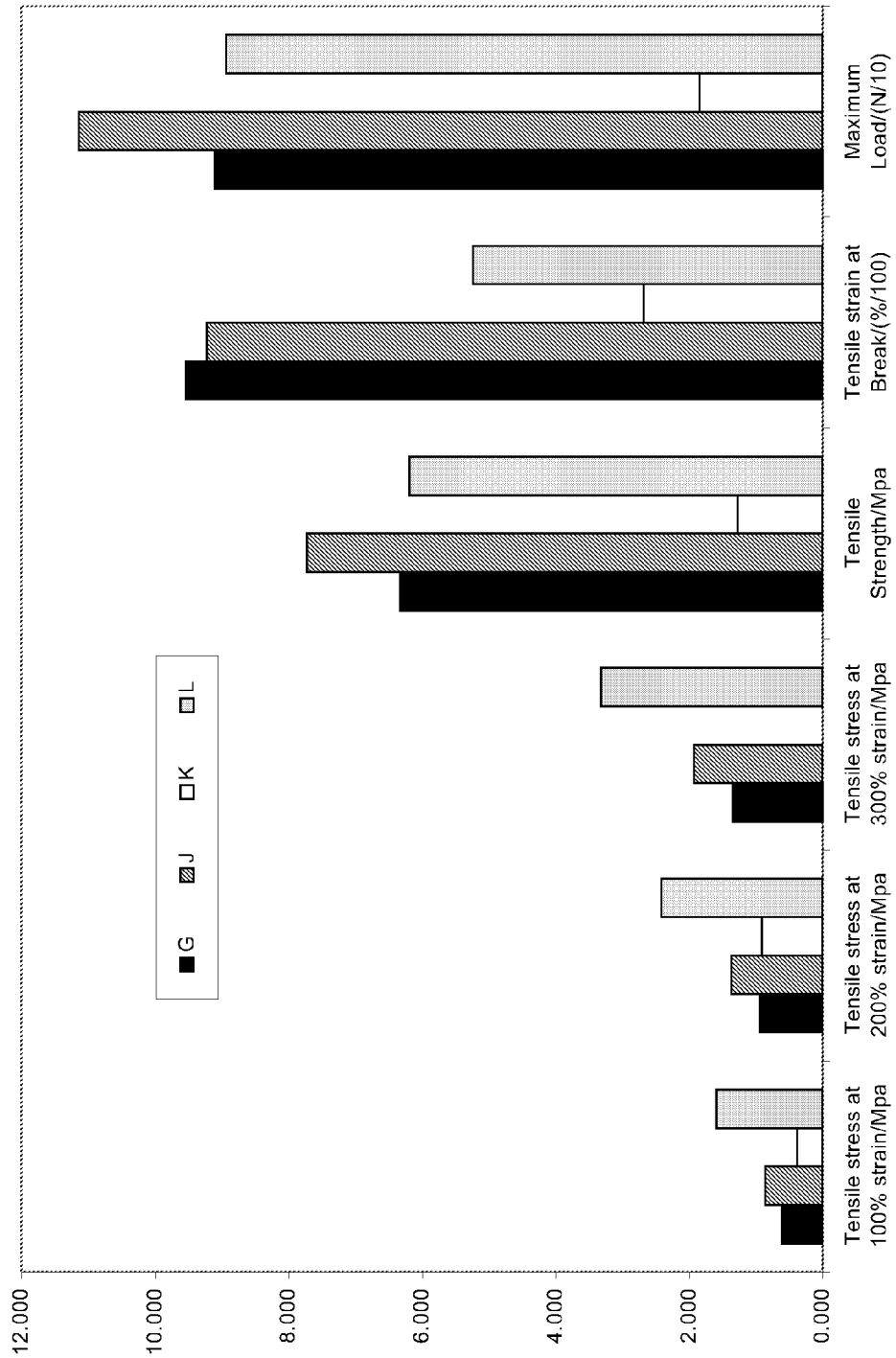
FIGS. 5 and 6 show mechanical properties of polyurethanes prepared using various catalysts.
Figure 6:
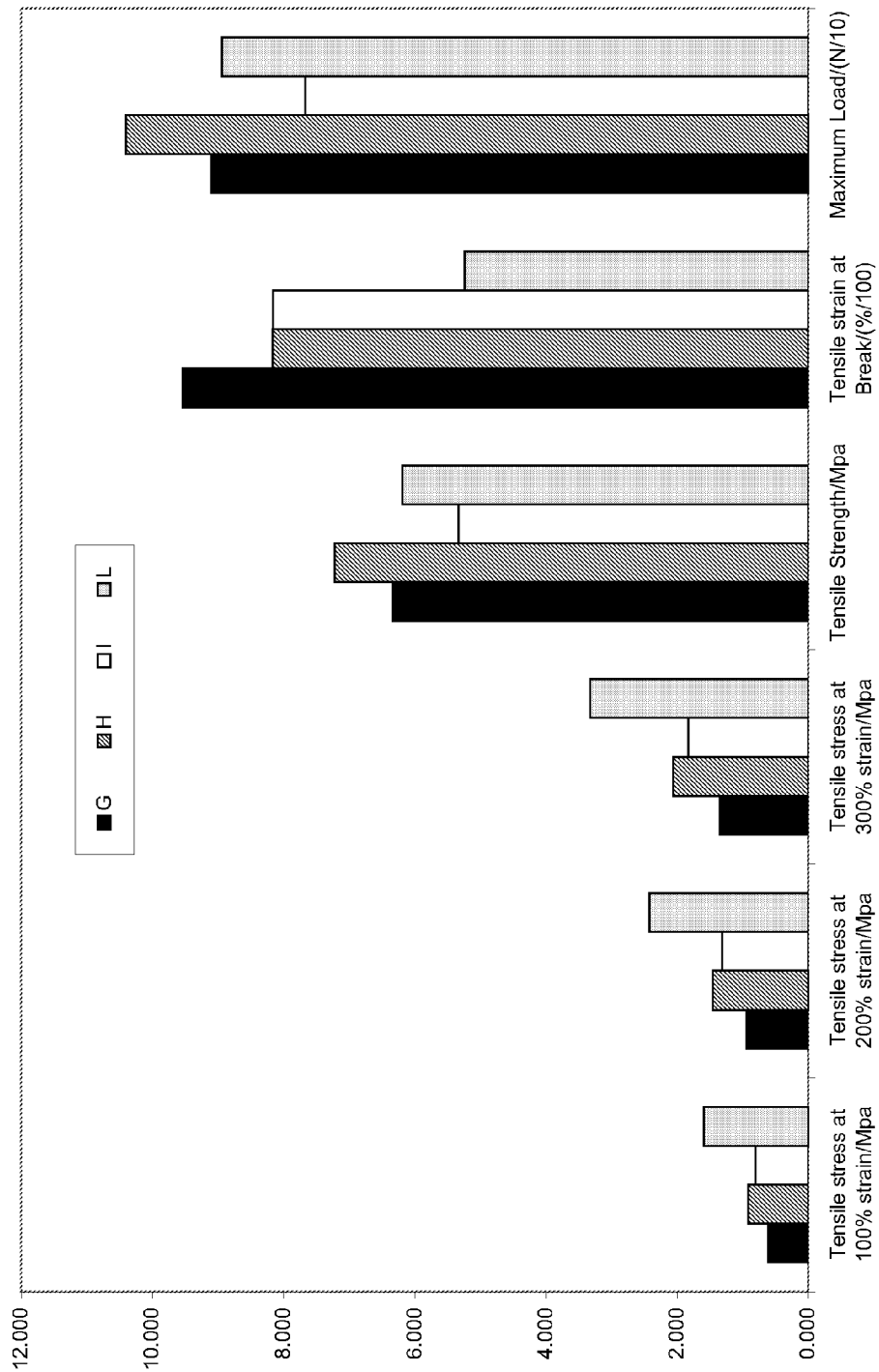

Samples of polyurethane elastomer for mechanical testing were prepared by reacting the polyol composition described in Example 7(a) to the prepolymer described in Example 7(b) at a ratio of 100 parts by weight of the polyol to 52 parts by weight of the prepolymer (index NCO:OH=1.1). Between 0.3-0.7 wt % (based on the weight of polyol+catalyst) of the catalyst composition shown in Table 4 was added to between 20-100 g of the polyol side, and the mixture was mixed on a centrifugal mixer for 30 seconds. The corresponding amount of prepolymer was then added to the polyol and mixed on a centrifugal mixer for another 30 seconds. The reaction mixture was then degassed under vacuum and cured in a mould at room temperature. The samples were then tested using an Instron™ mechanical testing instrument. The results from 6 tests were averaged and are plotted in FIGS. 5 and 6, with elastomer made using the mercury-containing catalyst shown for comparison.

TABLE 4

| Composition | Catalyst | Addition % |
|---|---|---|
| G | Cat 1 | 0.5 |
| H | Cat 1:P41 70:30 | 0.1 |
| *I | P41 | 0.3 |
| J | Cat 1:TMR3 90:10 | 0.15 |
| *K | TMR3 | 0.5 |
| *L | HgT535 | 0.2 |

*Compositions I, K and L are shown for comparison purposes.

Example 9

Tetraisopropyl titanate (TIPT) (28.42 g) was slowly added to N,N,N',N' tetra(hydroxy-2-ethyl)ethylenediamine (23.63 g) with constant mixing. The mixture became warm and a colourless liquid was produced. This solution was then diluted in 1,4-butanediol (16.73 g).

Example 10

Tetraisopropyl titanate (28.42 g) was slowly added to N,N,N',N' tetra(hydroxy-2-propyl)ethylenediamine (29.24 g) with constant mixing. The mixture became warm and a colourless liquid was produced. This solution was then diluted in diethylene glycol (DEG) (22.34 g).

Example 11

Tetraisopropyl titanate (28.42 g) was slowly added to N,N,N',N' tetra(hydroxy-2-butyl)ethylenediamine (38.85 g) with constant mixing. The mixture became warm and a colourless liquid was produced. This solution was then diluted in DEG (16.73 g).

Example 12

44.3 g of a solution of n-propyl zirconate in n-propyl alcohol (0.1 moles of zirconium) was slowly added to N,N,N',N' tetra(hydroxy-2-ethyl)ethylenediamine (23.631 g) with constant mixing. The mixture became warm and a colourless liquid was produced. This solution was then diluted in 1,3 propanediol (PDO) (12.07 g).

Example 13

44.3 g of a solution of n-propyl zirconate in n-propyl alcohol (0.1 moles of zirconium) was slowly added to N,N,N',N' tetra(hydroxy-2-propyl)ethylenediamine (29.242 g) with constant mixing. The mixture became warm and a colourless liquid was produced. This solution was then diluted in PDO (6.46 g).

Example 14

Ti(N,N,N',N'-(2-oxybutyl)$_3$(2-hydroxybutyl)ethylenediamine)(pentanedionato)

Acetylacetone (1 eq. 1.25 g) was slowly added to the solution made in Example 11 (10 g) with constant mixing, producing a yellow liquid. This solution was then further diluted in DEG (13.75 g). By 1 eq we mean that the amount of acetylacetone added used was equivalent to 1 mole of acetylacetone per mole of titanium and "eq" as used in other formulations herein has the same meaning, whereby the amount of the added compound is calculated per mole of metal.

Example 15

Ti(N,N,N',N'-(2-oxypropyl)$_3$(2-hydroxypropyl)ethylenediamine)(pentanedionato)

Acetylacetone (3.2 eq, 4 g) was slowly added to the solution made in Example 10 (10 g) with constant mixing, producing a yellow liquid. This solution was then further diluted in DEG (11 g).

Example 16

Acetylacetone (3.2 eq, 4 g) was slowly added to the solution made in Example 11 (10 g) with constant mixing, producing a yellow liquid. This solution was then further diluted in DEG (11 g).

Example 17

Acetylacetone (3.2 eq, 4 g) was slowly added to the solution made in Example 13 (10 g) with constant mixing, producing a yellow liquid. This solution was then further diluted in PDO (11 g).

Example 18

Ethyl acetoacetate (3.2 eq, 5.22 g) was slowly added to the solution made in Example 9 (10 g) with constant mixing, producing a pale yellow liquid. This solution was then further diluted in BDO (9.78 g).

Example 19

Ethyl acetoacetate (3.2 eq, 5.22 g) was slowly added to the solution made in Example 10 (10 g) with constant mixing, producing a pale yellow liquid. This solution was then further diluted in DEG (9.78 g).

Example 20

Salicylic acid (3.2 eq, 5.52 g) was slowly added to the solution made in Example 9 (10 g) with constant mixing, producing a red viscous liquid. This solution was then further diluted in BDO (9.48 g).

Example 21

Salicylic acid (3.2 eq, 5.52 g) was slowly added to the solution made in Example 12 (10 g) with constant mixing, producing an insoluble white solid. This solution was then further diluted in PDO (9.48 g).

Example 22

Mandelic acid (3.2 eq, 6.09 g) was slowly added to the solution made in Example 10 (10 g) with constant mixing, producing a colourless liquid. This solution was then further diluted in DEG (8.91 g).

Example 23

Mandelic acid (3.2 eq, 6.09 g) was slowly added to the solution made in Example 12 (10 g) with constant mixing, producing a pale yellow liquid. This solution was then further diluted in PDO (8.91 g).

Example 24

Isostearic acid (3.2 eq, 11.36 g) was slowly added to the solution made in Example 10 (10 g) with constant mixing, producing a pale yellow liquid. This solution was then further diluted in DEG (3.64 g).

Example 25

Butyl acid phosphate (3.2 eq, 7.29 g) was slowly added to the solution made in Example 9 (10 g) with constant mixing, slowly producing a white gel. This solution was then further diluted in BDO (7.71 g).

Example 26

2,2,6,6-tetramethyl-3,5-heptanedione (3.2 eq, 7.37 g) was slowly added to the solution made in Example 9 (10 g) with constant mixing, producing a pale yellow liquid. This solution was then further diluted in BDO (7.63 g).

Example 27

2,2,6,6-tetramethyl-3,5-heptanedione (3.2 eq, 7.37 g) was slowly added to the solution made in Example 12 (10 g) with constant mixing, producing a pale yellow liquid. This solution was then further diluted in PDO (7.63 g).

Example 28

Tetraisopropyl titanate (3.66 g, 12.9 mmol) was added slowly to N,N,N',N'-tetrakis-2-hydroxypropyl-ethylenediamine (3.76 g, 12.9 mmol) followed by acetylacetone (2.58 g, 25.8 mmol), with constant mixing to produce a yellow liquid. 2.00 g of this liquid was then blended with castor oil (18.00 g).

Example 29

Example 28 was repeated with the castor oil being replaced with rape-seed oil (18 g).

Example 30

10 g of Ti(TOPED) and 90 g castor oil were blended together to give a orange liquid.

Example 31

10 g of Ti(TOPED) and 90 g glycerol were blended together to give a yellow liquid.

Example 32

Tetraisopropyl titanate (3.66 g, 12.9 mmol) was added slowly to N,N,N',N'tetrakis2-hydroxypropyl-ethylenediamine (3.76 g, 12.9 mmol) with constant mixing. After the components had fully reacted, acetylacetone (2.58 g, 25.8 mmol) was added to form a yellow liquid. 2.00 g of this liquid was then blended with DEG (18 g) to make a catalyst.

Example 33

Example 32 was repeated with the DEG being replaced by PDO (18 g).

Example 34

Stability Trial

Polyol Blend
A polyol blend was made by blending the following ingredients:

| Component | Parts by weight |
| --- | --- |
| Caradol ™ 56-07 | 0.470 |
| Voranol ™ EP1900 | 0.470 |
| 1,4-butanediol | 0.060 |
| BYK ™ 085 (a silicone antifoam) | 0.001 |

Caradol is a trademark of Shell Chemicals. Voranol is a trademark of the Dow Chemical Company. BYK is a trademark of BYK-Chemie GmbH. The polyol blend contained 853 ppm of water.

Prepolymer
Flaked MDI (4215 g) was warmed to 60° C. under nitrogen and left until it was fully melted. Caradol 56-07 (2785 g) was then added slowly through a dropping funnel and left to react for 3 hours under nitrogen, with constant agitation, to form a prepolymer.

Test Procedure
A quantity of catalyst was added to 240 g of the polyol blend and mixed in with a laboratory mixer. The quantities used are shown in Table 5, expressed as weight in grams of composition as made in the referenced Example (including diluent, if present) added and as a percentage by weight of this composition in the polyol blend. The resulting mixture was split into 4 pots, each containing 57.35 g, which were stored at 60° C. After 2.5 hours (2 pots) or 7 days (2 pots) the pot was cooled to 25° C. and added to 32.65 g of the prepolymer at 25° C. and mixed in a centrifugal mixer for 30 seconds at 3000 rpm. The gel time was then measured using a Gardco™ GT-S-220 gel timer.

TABLE 5

| Catalyst | Amount % (g) | Average gel time after 2.5 hours (GT1) (seconds) | Average gel time after 7 days (GT2) (seconds) | $\frac{GT2 - GT1}{GT1} * 100$ (%) |
| --- | --- | --- | --- | --- |
| VERTEC TAA | 0.08% (0.19 g) | 452 | 2797 | 519 |
| Example 10 | 0.4% (0.96 g) | 266 | 326 | 22.6 |
| Example 11 | 0.4% (0.96 g) | 358 | 421 | 17.76 |
| Example 13 | 3.8% (9.0 g) | 250 | 307 | 22.85 |
| Example 14 | 2.0% (4.8 g) | 242 | 211 | −12.63 |
| Example 15 | 0.4% (0.96 g) | 724 | 577 | −20.30 |
| Example 18 | 1.1% (2.4 g) | 108 | 152 | 41.4 |
| Example 24 | 1.1% (2.4 g) | 232 | 280 | 20.69 |

The gel times, shown in Table 5, are taken from the time the centrifugal mixture was started and are the average gel time from 2 pots of polyol+catalyst mixture. VERTEC™ TAA was also used as a comparison catalyst. The variation in gel time between the polyol stored for 2.5 hours (GT1) and the polyol stored for 7 days (GT2) is shown as (GT2−GT1)*100%/GT1. A small variation indicates that the catalyst has remained stable during the 7 day storage period and is capable of producing gel times similar to that given after only 2.5 hours storage in the polyol.

Example 35

7.0 g of the catalyst made in Example 33 was blended with 3.0 g of DABCO TMR-3 to form a clear yellow liquid. The resulting catalyst composition was used at a concentration of 0.1% (0.059 g) in the polyol (59.2 g) which was reacted with the prepolymer (30.8 g) at an initial temperature of 36.6° C. The gel time was measured as 300 seconds.

Example 36

8.0 g of the catalyst made in Example 33 was blended with 2.0 g of DABCO TMR-3 to form a clear yellow liquid. The resulting catalyst composition was used at a concentration of 0.11% (0.065 g) in the polyol (59.2 g) which was reacted with the prepolymer (30.8 g) at an initial temperature of 38.6° C. The gel time was measured as 300 seconds.

Example 37

9.0 g of the catalyst made in Example 33 was blended with 1.0 g of DABCO TMR-3 to form a clear yellow liquid. The resulting catalyst composition was used at a concentration of 0.15% (0.089 g) in the polyol (59.2 g) which was reacted with the prepolymer (30.8 g) at an initial temperature of 36.0° C. The gel time was measured as 390 seconds.

Example 38

9.0 g of the catalyst of Example 32 was blended with 1.0 g of DABCO™ TMR-3 to form a clear yellow liquid and the resulting catalyst composition was analysed. The properties are shown in Table 6.

Example 39

8.0 g of the catalyst of Example 32 was blended with 2.0 g of Polycat™ 41 to form a red liquid which was analysed. The properties are shown in Table 6.

TABLE 6

| Property | Catalyst + TMR3 | Catalyst + P41 |
| --- | --- | --- |
| Specific gravity @ 25° C. (g ml$^{-1}$) | 1.140 | 1.071 |
| Viscosity (cP) | 38.9 | 70.2 |
| pH (10% in water) | 4.0 | 9.0 |
| Flash Point (° C.) | 57 | 64 |

Example 40

0.54 g of the catalyst made in Example 28 and 0.06 g of TMR3 was blended with 300 g of the polyol side of a commercial 2-part polyurethane elastomer formulation. The polyol contained 0.18% of the Catalyst 28 and 0.02% of the TMR3. The polyol was mixed with the isocyanate side of the formulation to form a polyurethane elastomer.

Example 41

2.4 g of the catalyst made in Example 28 was blended with 0.6 g of P41 and 12.0 g of castor oil and the resulting catalyst composition was blended with 300 g of the polyol side of a commercial 2-part polyurethane elastomer formulation. The polyol was mixed with the isocyanate side of the formulation to form a polyurethane elastomer.

Example 42

0.54 g of the catalyst made in Example 29 and 0.06 g of TMR3 was blended with a polyether polyol. The resulting polyol blend contained 0.18% of the Catalyst 28 and 0.02% of the TMR3. The polyol was mixed with a polyisocyanate formulation and cured to form a polyurethane elastomer.

Example 43

The catalyst compositions made in Examples 28, 29, 30 and 31 were each separately blended with a polyol. Each polyol blend was then successfully used to form a polyurethane elastomer by reaction with a polyisocyanate.

The invention claimed is:
1. A method of manufacturing a polyurethane compound consisting of mixing together
   (A) a polyol,
   (B) a polyisocyanate compound, and
   (C) a catalyst,
   and allowing the mixture to cure to form a polyurethane, wherein the catalyst consists of
   a) a metal-organic compound which is a complex of
      i) a metal selected from the group consisting of Ti, Zr, Hf, and Al; and
      ii) a multidentate organic ligand,
   wherein said multidentate organic ligand has
      (a) a number of anionic donor sites=x; and
      (b) a number of neutral donor sites, capable of forming a co-ordinate bond with the metal, =y;
   where x+y=from 5 to 8 and x is from 2 to 4;

said multidentate organic ligand molecule is of a size and conformation to enable each of the anionic donor sites and neutral donor sites to form a bond with the same metal atom; and wherein said multidentate organic ligand is derived from a ligand-forming compound having the following formula:

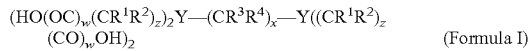
(Formula I)

in which:

Y is selected from P and N;

each $R^1$, $R^2$, $R^2$ and $R^4$ is independently selected from H, alkyl, aryl, substituted alkyl or substituted aryl;

each z is independently 1, 2, 3 or 4;

x represents the least number C atoms between the Y atoms and is 2 or 3;

each w is independently 0 or 1; and wherein (a) the catalyst is first mixed with the polyol to form polyol composition, and (b) the polyol composition is then reacted by mixing with the polyisocyanate compound; and wherein the mixing is continuous.

2. The method according to claim 1, wherein each z is 2 or 3.

3. The method according to claim 1, wherein x and each z is 2.

4. The method according to claim 1, wherein w=0.

5. The method according to claim 1, wherein the ligand-forming compound is selected from the group consisting of:

N,N,N',N'-tetrakis(2-hydroxyethyl)ethylenediamine,
N,N,N',N'-tetrakis(2-hydroxypropyl)ethylenediamine, and
N,N,N',N'-tetrakis(2-hydroxybutyl)ethylenediamine.

6. The method according to claim 1, wherein the metal-organic compound is in hydrated form.

7. A method of manufacturing a polyurethane compound consisting of mixing together (A) a polyol,
(B) a polyisocyanate compound, and
(C) a catalyst, and allowing the mixture to cure to form a polyurethane, wherein the catalyst consists of a) metal-organic compound which is a complex of
  i) a metal selected from the group consisting of Ti, Zr, Hf, and Al;
  ii) a multidentate organic ligand, and
  iii) a chelating ligands wherein said multidentate organic ligand has (a) a number of anionic donor sites=x; and
(b) a number of neutral donor sites, capable of forming a co-ordinate bond with the metal, =y;

where x+y=from 5 to 8 and x is from 2 to 4;

said multidentate organic ligand molecule is of a size and conformation to enable each of the anionic donor sites and neutral donor sites to form a bond with the same metal atom; and wherein said multidentate organic ligand is derived from a ligand-forming compound having the following formula:

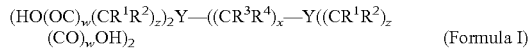
(Formula I)

in which:

Y is selected from P and N;

each $R^1$, $R^2$, $R^3$ and $R^4$ is independently selected from H, alkyl, aryl, substituted alkyl or substituted aryl;

each z is independently 1, 2, 3 or 4;

x represents the least number of C atoms between the Y atoms and is 2 or 3;

each w is independently 0 or 1; and wherein (a) the catalyst is first mixed with the polyol to form polyol composition, and (b) the polyol composition is then reacted by mixing with the polyisocyanate compound; and wherein the mixing is continuous.

8. The method according to claim 7, wherein said chelating ligand is derived from one or more compounds selected from the group consisting of beta-diketones, beta-ketoesters, beta-ketoamides, acid phosphates, phosphate esters, organic sulphonic acids, phosphoric acid, organic carboxylic acids, phenols and alpha-hydroxyacids.

9. A method of manufacturing a polyurethane compound consisting of mixing together (A) a polyol,
(B) a polyisocyanate compound, and
(C) a catalyst, and allowing the mixture to cure to form a polyurethane, wherein the catalyst consists of a) metal-organic compound which is a complex of
  i) a metal selected from the group consisting of Ti, Zr, Hf, and Al; and
  ii) a multidentate organic ligand,
b) a co-catalyst, said co-catalyst being an effective polyisocyanate trimerisation catalyst;

wherein said multidentate organic ligand has (a) a number of anionic donor sites=x; and
(b) a number of neutral donor sites, capable of forming a co-ordinate bond with the metal, =y;

where x+y=from 5 to 8 and x is from 2 to 4;

said multidentate organic ligand molecule is of a size and conformation to enable each of the anionic donor sites and neutral donor sites to form a bond with the same metal atom; and wherein said multidentate organic ligand is derived from a ligand-forming compound having the following formula:

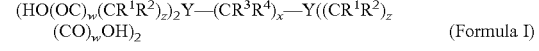
(Formula I)

in which:

Y is selected from P and N;

each $R^1$, $R^2$, $R^3$ and $R^4$ is independently selected from H, alkyl, aryl, substituted alkyl or substituted aryl;

each z is independently 1, 2, 3 or 4;

x represents the least number of C atoms between the Y atoms and is 2 or 3;

each w is independently 0 or 1; and wherein (a) the catalyst is first mixed with the polyol to form polyol composition, and (b) the polyol composition is then reacted by mixing with the polyisocyanate compound; and wherein the mixing is continuous.

10. The method according to claim 9, wherein said co-catalyst comprises at least one compound selected from the group consisting of an amine, an alkali metal or quaternary ammonium salt of an oxygen-containing acid or an alkyl ester thereof, an N,N-dialkylacetoacetamide, a 2,3-dialkyltetrahydropyrimidine and sodium glycinate.

11. A catalyst composition for manufacturing a polyurethane compound, wherein the composition consists of:

(a) a metal-organic compound which is a complex of
  (i) a metal selected from the group consisting of Ti, Zr, Hf, and Al, and (ii) a multidentate organic ligand;
wherein the multidentate organic ligand has
a) a number of anionic donor sites=x1; and
b) a number of neutral donor sites, capable of forming a co-ordinate bond with the metal, =y;
where x+y=from 5 to 8 and x is from 2 to 4;
said multidentate organic ligand molecule is of a size and conformation to enable each of the anionic donor sites and neutral donor sites to form a bond with the same metal atom; and
wherein said multidentate organic ligand is derived from a ligand-forming compound having the following formula:

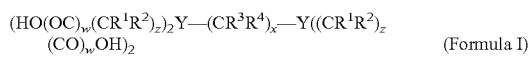  (Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1; and
(b) optionally a diluent; and
wherein (a) the catalyst composition is first mixed with a polyol to form polyol composition, and (b) the polyol composition is then reacted by mixing with the polyisocyanate compound for use in preparation of a polyurethane; and
wherein the mixing is continuous.

12. The catalyst composition according to claim 11 wherein said metal-organic compound is a compound of general formula:

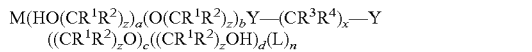

wherein M is a metal atom selected from the group consisting of Ti, Zr, Hf, and Al;
Y is selected from P and N;
each $R^1$, $R^2$, $R^3$ and $R^4$ is independently selected from the group consisting of H, alkyl, aryl, substituted alkyl and substituted aryl,
d and a are each 0 or 1,
b and c are each 1 or 2,
b+c=the valency of M,
a+b+c+d=4,
each z is independently 1, 2, 3 or 4;
x represents the least number of C atoms between the Y atoms and is 2 or 3;
n=1 or 2; and
L is a monodentate or bidentate ligand.

13. The catalyst composition according to claim 12, wherein L is derived from one or more compounds selected from the group consisting of beta-diketones, beta-ketoesters, beta-ketoamides, acid phosphates and phosphate esters, organic sulphonic acids, phosphoric acid, organic carboxylic acids, phenols and alpha-hydroxyacids.

14. The catalyst composition according to claim 11, wherein said metal-organic compound comprises at least one of:
Ti(N,N,N',N'-tetrakis(2-oxyalkyl)ethylenediamine),
Ti(N,N,N',N'-(2-oxyalkyl)$_3$(2-hydroxyalkyl)ethylenediamine)(pentanedionato),
Ti(N,N,N',N'-(2-oxyalkyl)$_3$(2-hydroxyalkyl)ethylenediamine)(ethylacetoacetato),
Ti(N,N,N',N'-(2-oxyalkyl)$_3$(2-hydroxyalkyl)ethylenediamine)(N,N-diethylacetoacetamido),
Ti(N,N,N',N'-(2-oxyalkyl)$_3$(2-hydroxyalkyl)ethylenediamine)(isostearate),
Ti(N N,N,N'-(2-oxyalkyl)$_3$(2-hydroxyalkyl)ethylenediamine)salicylate),
Ti(N,N,N',N'-(2-oxyalkyl)$_3$(2-hydroxyalkyl)ethylenediamine)(mandelate),
Ti(N,N,N',N'-(2-oxyalkyl)$_3$(2-hydroxyalkyl)ethylenediamine)(2,2,6,6-tetramethyl-3,5-heptanedionato),
Zr(N,N,N',N'-tetrakis(2-oxyalkyl)ethylenediamine),
Zr(N,N,N',N'-(2-oxyalkyl)$_3$(2-hydroxyalkyl)ethylenediamine)(pentanedionato),
Zr(N,N,N',N'-(2-oxyalkyl)$_3$(2-hydroxyalkyl)ethylenediamine)(ethylacetoacetato),
Zr(N,N,N',N'-(2-oxyalkyl)$_3$(2-hydroxyalkyl)ethylenediamine)(N,N-diethylacetoacetamido),
Zr(N,N,N',N'-(2-oxyalkyl)$_3$(2-hydroxyalkyl)ethylenediamine)(salicylate),
Zr(N,N,N',N'-(2-oxyalkyl)$_3$(2-hydroxyalkyl)ethylenediamine)(mandelate), and
Zr(N,N,N',N'-(2-oxyalkyl)$_3$(2-hydroxyalkyl)ethylenedamne(2,2,6,6-tetramethyl-3,5-heptanedionato),
where oxyalkyl is oxyethyl, oxypropyl or oxybutyl.

15. The catalyst composition according to claim 11, comprising from 1 to 20 parts by weight of the metal-organic compound.

16. A catalyst composition for manufacturing a polyurethane compound, wherein the composition consists of:
(a) a metal-organic compound which is a complex of
(i) a metal selected from the group consisting of Ti, Zr, Hf, and Al, and
(ii) a multidentate organic ligand;
wherein the multidentate organic ligand has
a) a number of anionic donor sites=x1; and
b) a number the neutral donor sites, capable of forming a co-ordinate bond with the metal, =y;
where x+y=from 5 to 8 and x is from 2 to 4;
said multidentate organic ligand molecule is of a size and conformation to enable each of the anionic donor sites and neutral donor sites to form a bond with the same metal atom; and
wherein said multidentate organic ligand is derived from a ligand-forming compound having the following formula:

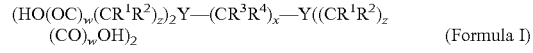  (Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1;
(b) optionally a diluent; and
(c) co-catalyst,
wherein (a) the catalyst composition is first mixed with a polyol to form polyol composition, and (b) the polyol composition is the reacted by mixing with the polyisocyanate compound for use in preparation of a polyurethane; and
wherein the mixing is continuous.

17. The catalyst composition according to claim 16, wherein said co-catalyst comprises a compound selected from the group consisting of an amine, an alkali metal or quaternary ammonium salt of an oxygen-containing acid or an alkyl ester thereof, an N,N-dialkylacetoacetamide, a 2,3-dialkyltetrahydropyrimidine and sodium glycinate.

18. The catalyst composition according to claim 11, wherein said diluent is selected from the group consisting of water, an alcohol, a diol, a polyol, another protic solvent and a glycerol-based oil.

19. The catalyst composition according to claim 11, comprising from 5-100% by weight of said metal-organic compound and from 0-90% by weight of said diluent.

20. The catalyst composition according to claim 11, wherein said metal is selected from the group consisting of titanium, zirconium, hafnium and aluminium.

21. The method according to claim 1, wherein the metal-organic compound has following formula II

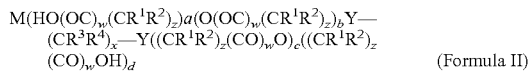 (Formula II)

in which

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, and each w is independently 0 or 1.

22. The method as claimed in claim 6, wherein the hydrated metal-organic compound has a formula

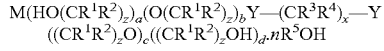

in which

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, n=1 or 2, $R^5$ is hydrogen, an alkyl group or a hydroxy-functionalised alkyl group.

23. The method as claimed in claim 7, wherein said metal-organic compound comprises a compound of formula:

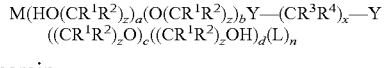

wherein

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, n=1 or 2, L is a monodentate or bidentate ligand.

24. The catalyst composition as claimed in claim 11, wherein said metal-organic compound has a following formula II

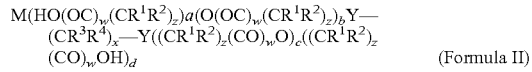 (Formula II)

in which

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, and each w is independently 0 or 1.

25. The catalyst composition according to claim 11, wherein said metal-organic compound is in hydrated form, and is of a formula

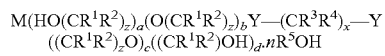

in which

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, n=1 or 2, $R^5$ is hydrogen, an alkyl group or a hydroxy-functionalised alkyl group.

26. The catalyst composition according to claim 11, wherein said metal-organic compound comprises further chelating ligands, and is of a formula

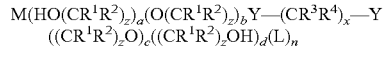

wherein

M is a metal atom selected from Ti, Zr, Hf, Al, Fe and Sn,

Y is selected from P and N, each $R^1$, $R^2$, $R^3$ and $R^4$ is independently selected from H, alkyl, aryl, substituted alkyl or substituted aryl, d and a are each 0 or 1, b and c are each 1 or 2, b+c=the valency of M, a+b+c+d=4, each z is independently 1, 2, 3 or 4, x represents the least number of C atoms between the Y atoms and is 2 or 3, n=1 or 2, L is a monodentate or bidentate ligand.

27. The method according to claim 1, wherein the mixing of the polyol and the catalyst to form the polyol composition, and the reaction by mixing the polyol composition and the polyisocyanate compound is done in a mixer.

28. The catalyst composition according to claim 11, wherein the mixing of the polyol and the catalyst to form the polyol composition, and the reaction by mixing the polyol composition and the polyisocyanate compound is done in a mixer.

29. The catalyst composition according to claim 16, wherein the composition comprises from 1 to 20 parts by weight of the co-catalyst.

30. A method of manufacturing a polyurethane compound consisting of mixing together
(A) a polyol,
(B) a polyisocyanate compound, and
(C) a catalyst,
and allowing the mixture to cure to form a polyurethane, wherein the catalyst consists of
a) a metal-organic compound which is a complex of
  i) a metal selected from the group consisting of Ti, Zr, Hf, and Al; and
  ii) a multidentate organic ligand,
wherein said multidentate organic ligand has
(a) a number of anionic donor sites=x; and
(b) a number of neutral donor sites, capable of forming a co-ordinate bond with the metal, =y;
where x+y=from 5 to 8 and x is from 2 to 4;
said multidentate organic ligand molecule is of a size and conformation to enable each of the anionic donor sites and neutral donor sites to form a bond with the same metal atom; and
wherein said multidentate organic ligand is derived from a ligand-forming compound having the following formula:

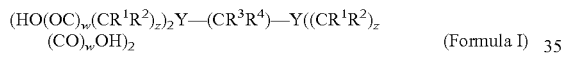

(Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1; and
wherein (a) the catalyst, (b) the polyol and (c) the polyisocyanate compound are mixed together and reacted; and wherein the mixing is continuous.

31. A catalyst composition for manufacturing a polyurethane compound, wherein the composition consists of:
(a) a metal-organic compound which is a complex of
  (i) a metal selected from the group consisting of Ti, Zr, Hf, and Al, and
  (ii) a multidentate organic ligand;
    wherein the multidentate organic ligand has
    a) a number of anionic donor sites=x1; and
    b) a number of neutral donor sites, capable of forming a co-ordinate bond with the metal, =y;
    where x+y=from 5 to 8 and x is from 2 to 4;
    said multidentate organic ligand molecule is of a size and conformation to enable each of the anionic donor sites and neutral donor sites to form a bond with the same metal atom; and
    wherein said multidentate organic ligand is derived from a ligand-forming compound having the following formula:

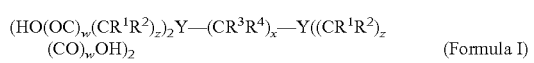

(Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1;
and
(b) optionally a diluent; and
wherein (a) the catalyst, (b) the polyol and (c) the polyisocyanate compound are mixed together and reacted; and wherein the mixing is continuous.

32. A method of manufacturing a polyurethane compound consisting of mixing together
(A) a polyol,
(B) a polyisocyanate compound, and
(C) a catalyst,
and allowing the mixture to cure to form a polyurethane, wherein the catalyst consists of
a) a metal-organic compound which is a complex of
  i) a metal selected from the group consisting of Ti, Zr, Hf, and Al; and
  ii) a multidentate organic ligand,
wherein said multidentate organic ligand has
(a) a number of anionic donor sites=x; and
(b) a number of neutral donor sites, capable of forming a co-ordinate bond with the metal, =y;
where x+y=from 5 to 8 and x is from 2 to 4;
said multidentate organic ligand molecule is of a size and conformation to enable each of the anionic donor sites and neutral donor sites to form a bond with the same metal atom; and
wherein said multidentate organic ligand is derived from a ligand-forming compound having the following formula:

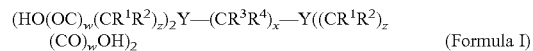

(Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1; and
wherein (a) the catalyst is mixed with (b) the polyol and (c) the polyisocyanate compound separately, and resulted mixtures are mixed together and reacted; and wherein the mixing is continuous.

33. A catalyst composition for manufacturing a polyurethane compound, wherein the composition consists of:
(a) a metal-organic compound which is a complex of
  (i) a metal selected from the group consisting of Ti, Zr, Hf, and Al, and
  (ii) a multidentate organic ligand;
    wherein the multidentate organic ligand has
    a) a number of anionic donor sites=x1; and
    b) a number of neutral donor sites, capable of forming a co-ordinate bond with the metal, =y;
    where x+y=from 5 to 8 and x is from 2 to 4;
    said multidentate organic ligand molecule is of a size and conformation to enable each of the anionic donor sites and neutral donor sites to form a bond with the same metal atom; and wherein said multidentate organic ligand is derived from a ligand-forming compound having the following formula:

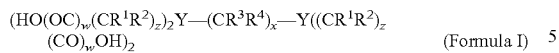

(Formula I)

in which:
Y is selected from P and N;
each $R^1$, $R^2$, $R^3$ and $R^4$ is independently selected from H, alkyl, aryl, substituted alkyl or substituted aryl;
each z is independently 1, 2, 3 or 4;
x represents the least number of C atoms between the Y atoms and is 2 or 3;
each w is independently 0 or 1;
and
(b) optionally a diluent; and
wherein (a) the catalyst is mixed with (b) the polyol and (c) the polyisocyanate compound separately, and resulted mixtures are mixed together and reacted; and wherein the mixing is continuous.

* * * * *

UNITED STATES PATENT AND TRADEMARK OFFICE
CERTIFICATE OF CORRECTION

PATENT NO. : 8,829,145 B2  
APPLICATION NO. : 12/665377  
DATED : September 9, 2014  
INVENTOR(S) : Arran Alexander Dickon Tulloch et al.

Page 1 of 1

It is certified that error appears in the above-identified patent and that said Letters Patent is hereby corrected as shown below:

In the Claims

In Column 19, line 48, replace "ligands" with --ligand--

In Column 19, lines 62-63, replace  
"$(HO(OC)_w(CR^1R^2)_z)_2Y-((CR^3R^4)_x-Y((CR^1R^2)_z(CO)_wOH)_2$" with  
--$(HO(OC)_w(CR^1R^2)_z)_2Y-(CR^3R^4)_x-Y((CR^1R^2)_z(CO)_wOH)_2$--

In Column 22, lines 5-6, replace  
"Ti(N  N,N,N'-(2-oxyalkyl)$_3$(2-hydroxyalkyl)ethylenediamine)salicylate)," with  
--Ti(N,N,N',N'-(2-oxyalkyl)$_3$(2-hydroxyalkyl)ethylenediamine)(salicylate),--

In Column 22, after line 17, insert  
--Zr(N,N,N',N'-(2-oxyalkyl)$_3$(2-hydroxyalkyl)ethylenediamine)(isostearate),--

In Column 22, lines 22-23, replace  
"Zr(N,N,N',N'-(2-oxyalkyl)$_3$(2-hydroxyalkyl)ethylenedamne(2,2,6,6-tetramethyl-3,5-heptanedionato)," with --Zr(N,N,N',N'-(2-oxyalkyl)$_3$(2-hydroxyalkyl)ethylenediamine)(2,2,6,6-tetramethyl-3,5-heptanedionato),--

Signed and Sealed this  
Thirtieth Day of December, 2014

Michelle K. Lee  
*Deputy Director of the United States Patent and Trademark Office*